(12) United States Patent
Orr

(10) Patent No.: US 9,095,464 B2
(45) Date of Patent: Aug. 4, 2015

(54) SLOTTED PUSHER ROD FOR FLEXIBLE DELIVERY SYSTEM

(75) Inventor: David E. Orr, Piedmont, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 64 days.

(21) Appl. No.: 13/379,962

(22) PCT Filed: Jun. 29, 2010

(86) PCT No.: PCT/US2010/040384
§ 371 (c)(1),
(2), (4) Date: Jan. 26, 2012

(87) PCT Pub. No.: WO2011/008538
PCT Pub. Date: Jan. 20, 2011

(65) Prior Publication Data
US 2012/0136425 A1    May 31, 2012

Related U.S. Application Data

(60) Provisional application No. 61/221,389, filed on Jun. 29, 2009.

(51) Int. Cl.
*A61F 2/06* (2013.01)
*A61F 2/966* (2013.01)
(Continued)

(52) U.S. Cl.
CPC . *A61F 2/966* (2013.01); *A61F 2/95* (2013.01); *A61F 2002/9511* (2013.01); *A61F 2002/9517* (2013.01); *A61F 2250/0018* (2013.01); *A61F 2250/0029* (2013.01); *A61M 25/0054* (2013.01)

(58) Field of Classification Search
CPC ............. A61M 25/0054; A61M 25/0138; A61M 25/0043; A61M 25/0051; A61M 25/0053; A61F 2/95; A61F 2/966; A61F 2250/0018
USPC ........ 623/1.11–1.13, 1.23; 606/108; 600/139, 600/141; 464/78; 138/118, 121
See application file for complete search history.

(56) References Cited

U.S. PATENT DOCUMENTS 3,844,137 A * 10/1974 Zugel ............................. 464/78
4,790,819 A    12/1988 Li et al.
5,322,064 A *  6/1994 Lundquist .................... 600/381
(Continued)

FOREIGN PATENT DOCUMENTS

EP    0812579    12/1997
EP    1208816    5/2002
(Continued)

OTHER PUBLICATIONS

International Search Report for PCT/US2010/040384 mailed Oct. 26, 2010, 4 pgs.
(Continued)

*Primary Examiner* — Katherine M Shi
(74) *Attorney, Agent, or Firm* — Brinks Gilson & Lione

(57) ABSTRACT

A delivery system for an intraluminal medical device comprises an elongate tubular sheath 20 and an elongate tubular pusher 50 slidably disposed within a lumen of the sheath and having a flexible configuration due to circumferentially-extending fins 154 along its exterior surface. The spacing and/or the size of the fins 154 may vary along the pusher 50. Different regions of the pusher 50 may be of materials with different flexibility.

20 Claims, 20 Drawing Sheets

(51) Int. Cl.
*A61F 2/95* (2013.01)
*A61M 25/00* (2006.01)

(56) References Cited

U.S. PATENT DOCUMENTS

| | | | |
|---|---|---|---|
| 5,562,641 | A | 10/1996 | Flomenblit et al. |
| 5,669,936 | A | 9/1997 | Lazarus |
| 5,782,907 | A | 7/1998 | Frantzen et al. |
| 5,843,051 | A | 12/1998 | Adams et al. |
| 6,022,343 | A | 2/2000 | Johnson et al. |
| 6,165,214 | A | 12/2000 | Lazarus |
| 6,592,520 | B1 | 7/2003 | Peszynski et al. |
| 6,852,116 | B2 | 2/2005 | Leonhardt et al. |
| 6,962,605 | B2 | 11/2005 | Cosgrove et al. |
| 7,014,653 | B2 | 3/2006 | Ouriel et al. |
| 7,037,316 | B2 | 5/2006 | McGuckin, Jr. et al. |
| 7,125,412 | B2 | 10/2006 | Shifrin et al. |
| 7,316,708 | B2 | 1/2008 | Gordon et al. |
| 2004/0010243 | A1 | 1/2004 | Klint |
| 2004/0098079 | A1* | 5/2004 | Hartley et al. ............... 623/1.11 |
| 2005/0004660 | A1 | 1/2005 | Rosenbluth et al. |
| 2005/0182475 | A1 | 8/2005 | Jen et al. |
| 2006/0100687 | A1* | 5/2006 | Fahey et al. .................. 623/1.11 |
| 2006/0135961 | A1* | 6/2006 | Rosenman et al. ........... 606/108 |
| 2006/0189896 | A1* | 8/2006 | Davis et al. .................. 600/585 |
| 2006/0235502 | A1* | 10/2006 | Belluche et al. ............. 623/1.11 |
| 2007/0106313 | A1 | 5/2007 | Golden et al. |
| 2007/0225746 | A1* | 9/2007 | Lee et al. ...................... 606/194 |
| 2008/0065204 | A1 | 3/2008 | Macoviak et al. |
| 2008/0114435 | A1 | 5/2008 | Bowe |

FOREIGN PATENT DOCUMENTS

| | | |
|---|---|---|
| EP | 1656963 | 5/2006 |
| EP | 1716822 | 11/2006 |
| WO | WO2007008829 | 1/2007 |
| WO | WO2008151204 | 12/2008 |

OTHER PUBLICATIONS

Written Opinion for PCT/US2010/040384 mailed Oct. 26, 2010, 7 pgs.
International Preliminary Report on Patentability for PCT/US2010/040384 issued Jan. 4, 2012, 8 pgs.

* cited by examiner

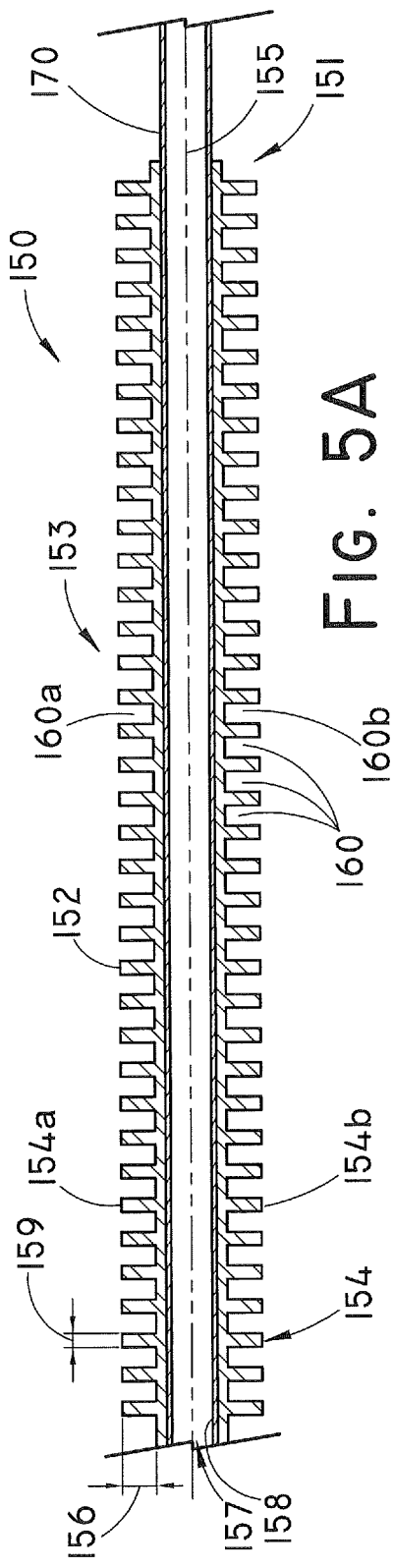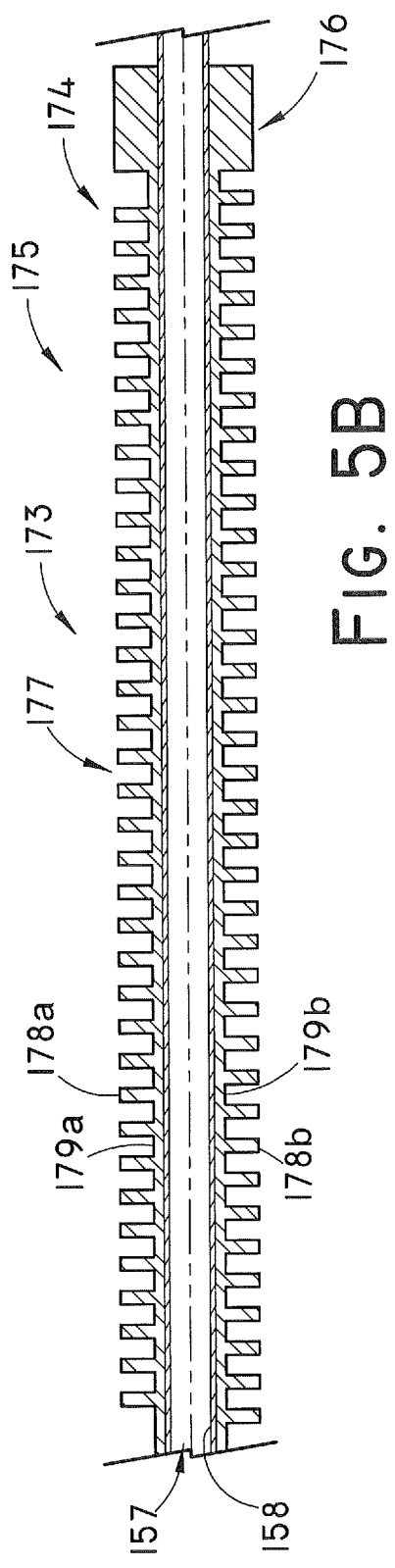

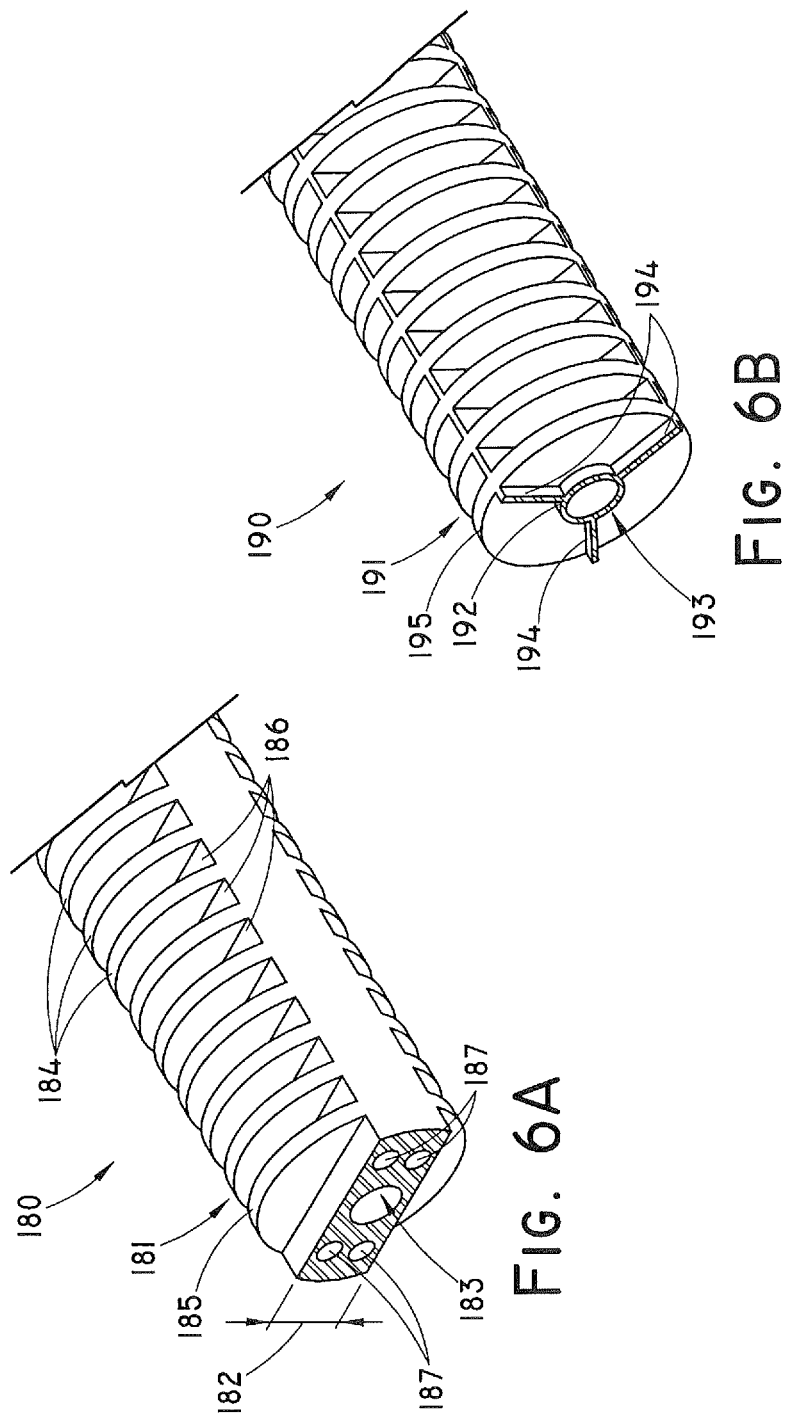

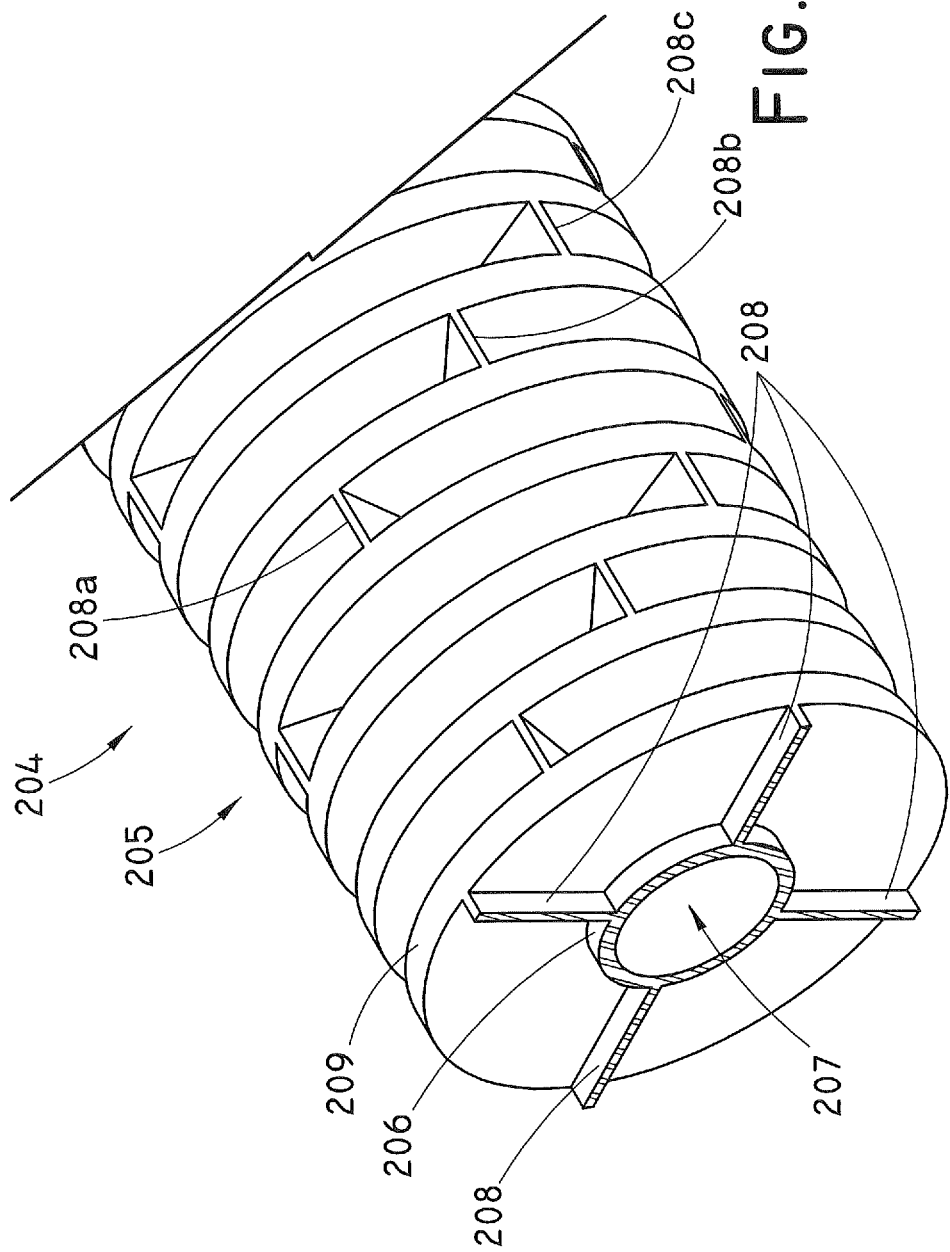

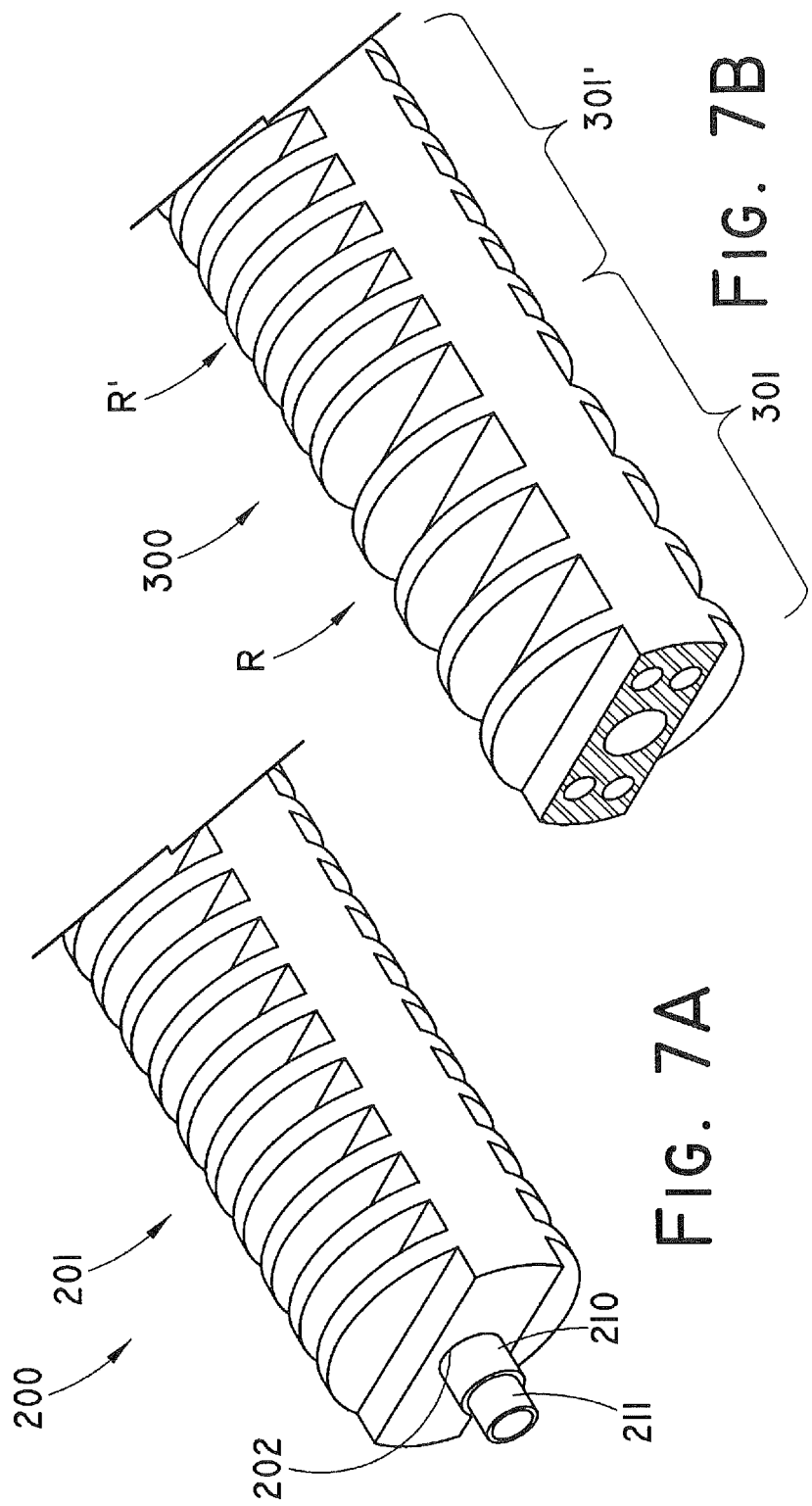

ized configuration. Once the
SLOTTED PUSHER ROD FOR FLEXIBLE DELIVERY SYSTEM

RELATED APPLICATIONS

The present patent document is a §371 filing based on PCT Application Serial No. PCT/US2010/040384, filed Jun. 29, 2010 (and published as WO 2011/008538 A1 on Jan. 20, 2011), designating the United States and published in English, which claims the benefit of the filing date under 35 U.S.C. §119(e) of Provisional U.S. Patent Application Ser. No. 61/221,389, filed Jun. 29, 2009. All of the foregoing applications are hereby incorporated by reference in their entirety.

This application claims the benefit of provisional U.S. Patent Application Ser. No. 61/221,389, filed Jun. 29, 2009, which is incorporated herein by reference in its entirety.

TECHNICAL FIELD

This application relates to a medical device, and, in particular, to a system for delivering a medical device.

BACKGROUND ART

The deployment of a medical device, such as an intraluminal prosthesis, into the lumen of a patient from a remote location by the use of a delivery device is generally known. Radially-expandable prostheses can be used, for example, to repair diseased and damaged aorta such as abdominal aortic aneurysms and thoracic aortic aneurysms. For example, a stent-graft may be loaded onto a delivery and deployment device and percutaneously inserted into the body lumen of a patient in a radially-compressed configuration. Once the prosthesis is in a proper position, it may be released so that it can radially expand to engage the walls of the body lumen. Exemplary expandable prostheses may be balloon-expandable, self-expanding, or both.

In general, delivery and deployment devices for intraluminal prostheses may include means for retaining and releasing the prosthesis into the body lumen. For example, such a device may include a cover or sheath for radially retaining the prosthesis in a compressed configuration. A pusher may be provided for pushing the sheath and the prosthesis into the body lumen and for delivering the device into a desired position. To deploy the prosthesis, the sheath may be withdrawn over the pusher and the prosthesis, thereby causing the prosthesis to become exposed and to expand into the body lumen.

There is currently a demand for delivery devices that are flexible and that are capable of negotiating or tracking complex and tortuous body lumina, for example the aortic arch. Such devices should exhibit high axial flexibility or trackability. One solution to improve the trackability of such delivery systems includes designing delivery system components out of generally flexible materials. For example, the sheath may comprise a generally flexible material, such as a low-durometer polyethylene or polytetrafluoroethylene (PTFE). U.S. Patent App. No. 2008/0114435 discloses a flexible delivery system comprising a pusher having at least one generally helical score in the exterior surface thereof to provide enhanced flexibility.

While it may be practical to use highly flexible materials for some applications, such as the introducer sheath, their use may be impractical for other applications, such as the pusher. The pusher must possess a high degree of pushability and therefore must, in general, possess high column strength, particularly when it is used to push a prosthesis within the introducer sheath. In general, soft and flexible materials may not possess sufficient structural integrity or strength for pusher applications. To this end, prior art pushers have been provided that are generally rigid and consequently have poor trackability.

There are many disadvantages of using a rigid pusher. For example, rigid pushers may preclude intraluminal intervention for patients with highly complex and tortuous body lumina. Also, rigid materials may possess poor kink-resistance and therefore may be susceptible to damage. The use of rigid pushers may also adversely affect the integrity of other system components, for example the sheath. For example, a relatively flexible sheath may bend or kink in the transition region between the prosthesis and a relatively rigid pusher. Accordingly, there is a present need in the art for an intraluminal prosthesis delivery and deployment system that addresses these and other problems.

DISCLOSURE OF THE INVENTION

According to a first aspect of the present invention, there is provided a delivery system for an intraluminal medical device, the system comprising: an elongate tubular sheath having a proximal end, a distal end, and a sheath lumen; an elongate tubular pusher slidably disposed within the sheath lumen, the pusher having a proximal end, a distal end, an exterior surface, and a lumen defining an interior surface; the pusher exterior surface comprising a slotted configuration having a plurality of fins and a plurality of interspaces separating the fins.

The slotted configuration is arranged to provide enhanced flexibility to the pusher.

In a preferred system, the distal end of the pusher comprises a dilator having a tapered distal end.

In one preferred embodiment, the pusher comprises a first material along a first portion thereof, and a second material along a second portion thereof, the first material being more flexible than the second material, and where the second portion of the pusher comprises an exterior surface having a slotted configuration. The slotted configuration is arranged to provide enhanced flexibility to the second portion of the pusher.

The system may comprise an elongate inner sheath fixably disposed within the pusher lumen between the proximal and distal pusher ends. In such an arrangement, the inner sheath preferably comprises a flexible plastic material and the pusher comprises a material that is more rigid than the inner sheath material.

The system may comprise a guide cannula having a proximal end and a distal end, the guide cannula being disposed within the lumen of the pusher and configured to receive the intraluminal medical device over a distal portion thereof.

According to a second aspect of the present invention, there is provided a delivery system for an intraluminal medical device, the system comprising: an elongate tubular sheath having a proximal end, a distal end, and a sheath lumen; an elongate tubular pusher slidably disposed within the sheath lumen, the pusher having a proximal end, a distal end, an exterior surface, and a lumen defining an interior surface; a radially-expandable intraluminal prosthesis disposed in a compressed configuration within a distal portion of the sheath lumen, where the pusher is configured to push the prosthesis distally within the sheath lumen when the sheath is slid proximally in relation thereto; an elongate inner sheath fixedly disposed within the pusher lumen between the proximal and distal pusher ends, the inner sheath comprising a flexible plastic material and the pusher comprising a material that is more rigid than the inner sheath material; a limiting member for limiting the proximal displacement of the sheath relative to the pusher, thereby limiting distal retraction of the pusher from the sheath lumen; a guide cannula having a proximal end and a distal end, the guide cannula disposed within the lumen of the pusher and configured to receive the expandable prosthesis over a distal portion thereof; a haemostatic seal for controlling blood loss through the pusher; the pusher exterior surface comprising a slotted configuration having a plurality of fins and a plurality of interspaces separating the fins, and further comprising no ribs, one rib, two ribs, three ribs, or four ribs, where the slotted configuration is selected from the group consisting of aligned slotted configurations, alternating slotted configurations, offset slotted configurations, spiral slotted configurations, and stepped slotted configurations; the plurality of fins comprising a radial depth that is less than or equal to the thickness of the pusher wall defined by the interior and exterior surfaces of the pusher.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

FIG. 5A is a side perspective view of a pusher of a delivery system in accordance with the present invention;

FIG. 5B is a side perspective view of a pusher of a delivery system in accordance with the present invention;

FIG. 6A is an end cross-sectional view of a pusher of a delivery system in accordance with the present invention;

FIG. 6B is an end cross-sectional view of a pusher of a delivery system in accordance with the present invention;

FIG. 6C is an end cross-sectional view of a pusher of a delivery system in accordance with the present invention;

FIG. 7A is an end cross-sectional view of a pusher of a delivery system in accordance with the present invention;

FIG. 7B is a sectional view of a pusher according to an aspect of the disclosure;

DETAILED DESCRIPTION

The present disclosure provides a delivery system for an intraluminal medical device. Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

DEFINITIONS

"Prosthesis" means any replacement for a body part or for a function of that body part, or any device that enhances or adds functionality to a physiological system.

"Proximal" and "proximally" means a position, direction, or orientation that is generally away from the patient (closest to the surgeon).

"Distal" or "distally" means a position, direction, or orientation that is generally toward the patient (away from the surgeon).

"Biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

"Comprise" and "include" and variations such as "comprising" and "including" imply the inclusion of an item or group of items, but not the exclusion of any other item or group of items.

Delivery System

Figure 1:
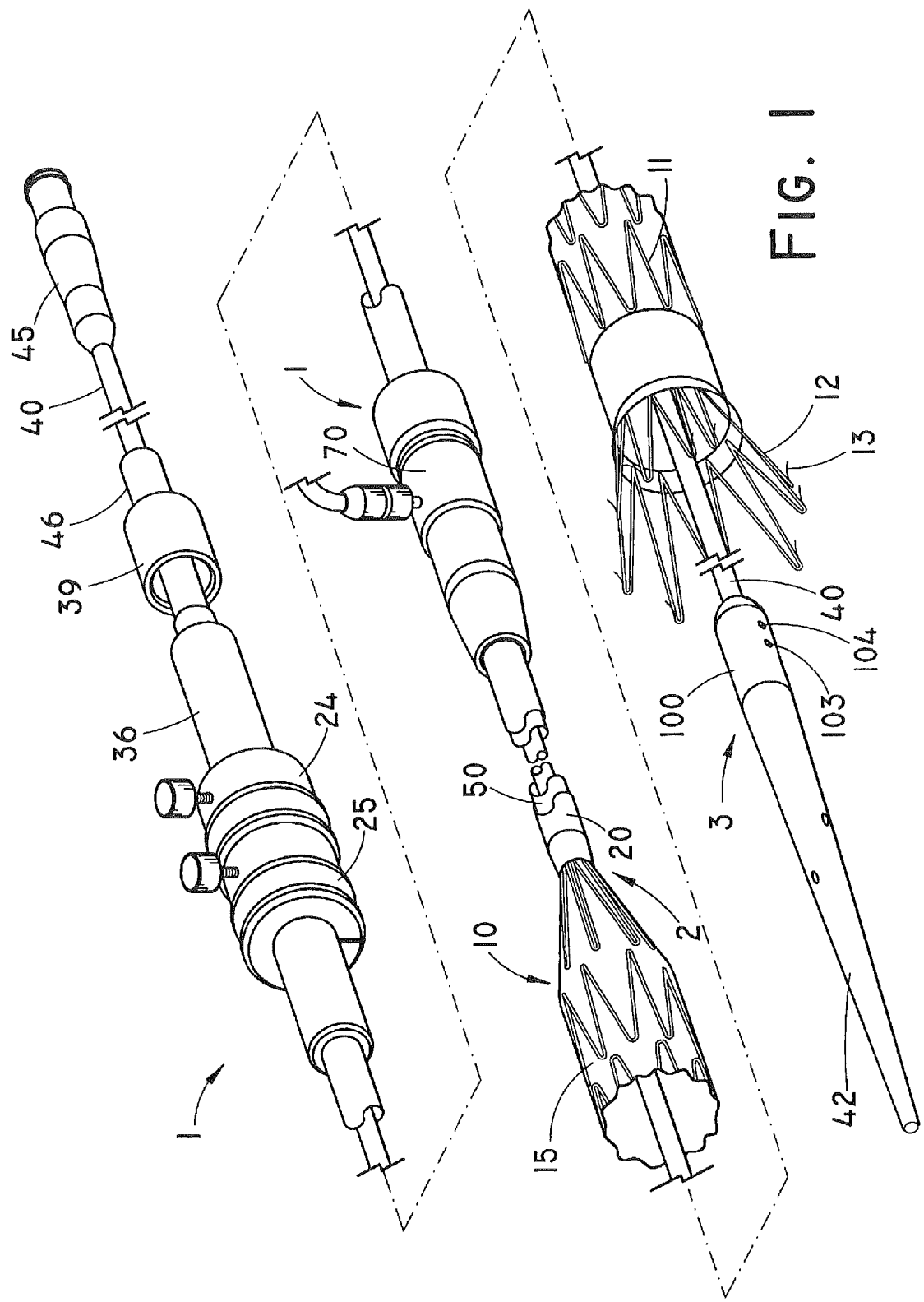
FIG. 1 is a perspective view of a delivery and deployment device employing a delivery system in accordance with the present invention.

FIG. 1 shows a delivery system for an intraluminal medical device; in particular, a system for delivering and deploying an intraluminal prosthesis 10 in a lumen of a patient during a medical procedure. The system includes an external manipulation section 1, a proximal positioning mechanism or attachment region 2, and a distal positioning mechanism or attachment region 3. During a medical procedure to deploy the prosthesis 10, the proximal and distal attachment regions 2 and 3 will travel through the lumen to a desired deployment site. The external manipulation section 1, which is acted upon by a user to manipulate the delivery and deployment device, remains outside of the patient throughout the procedure.

The prosthesis 10 may comprise a tubular graft material 15, such as Dacron. The prosthesis 10 may additionally or alternatively comprise a stent 11. The stent 11 may be self-expanding and cause the prosthesis 10 to expand when released from the delivery and deployment device. The stent 11 may be coupled to an interior or an exterior surface of the graft material 15. The prosthesis 10, as shown in FIG. 1, comprises a graft material 15 and a plurality of self-expanding stents 11.

The prosthesis 10 may optionally include a bare wire stent 12 disposed on an end of the prosthesis. The bare wire stent 12 expands and engages the body lumen, thereby anchoring the prosthesis 10 and preventing the prosthesis 10 from moving after implantation. As shown in FIG. 1, the stent 12 includes a self-expanding zigzag stent. The stent 12 may comprise anchoring means, for example barbs 13, that are configured to grasp the walls of the body lumen. Stents 11, 12 may comprise any suitable biocompatible material, including stainless steel and nitinol.

Figure 8:
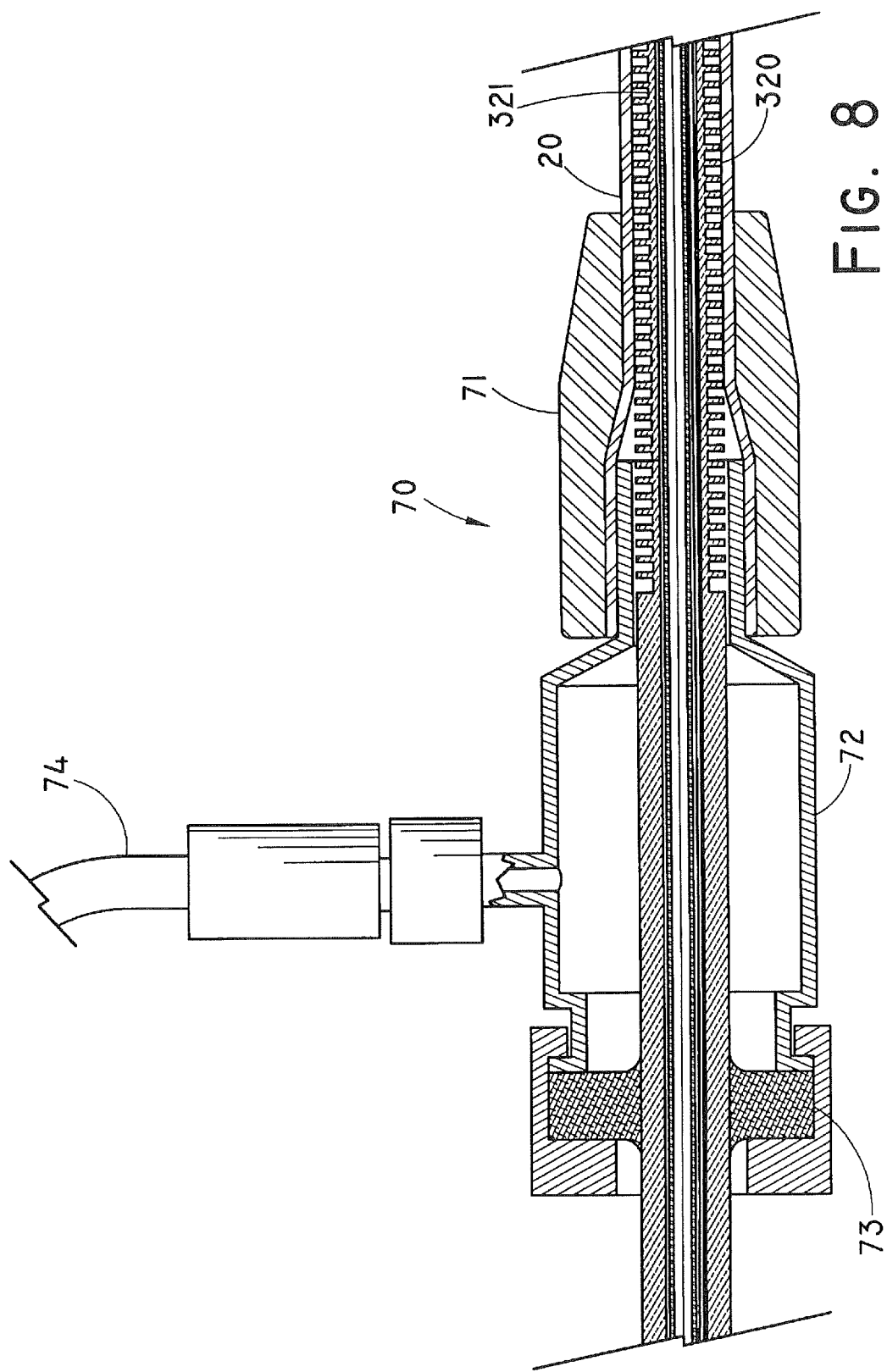
FIG. 8 is a sectional view of a portion of the delivery and deployment device of FIG. 1 around a haemostatic seal.

The prosthesis 10 is retained on a distal portion of the delivery and deployment device by sheath 20. Sheath 20 comprises a generally elongate tubular body having a lumen 21. The sheath 20 extends proximally to the manipulation region 1, as shown in FIG. 8. The prosthesis 10 is disposed within the lumen 21 of the sheath 20 in a radially-compressed configuration. The sheath 20 preferably comprises a flexible material so that in use it is able to negotiate complex and tortuous inner body lumina. The sheath 20 may also comprise a lubricious or slippery material to facilitate withdrawal of the sheath from the prosthesis 10 during delivery. Accordingly, the sheath 20 may comprise a biocompatible plastic such as PTFE, polyethylene, nylon, or the like.

Figure 2:
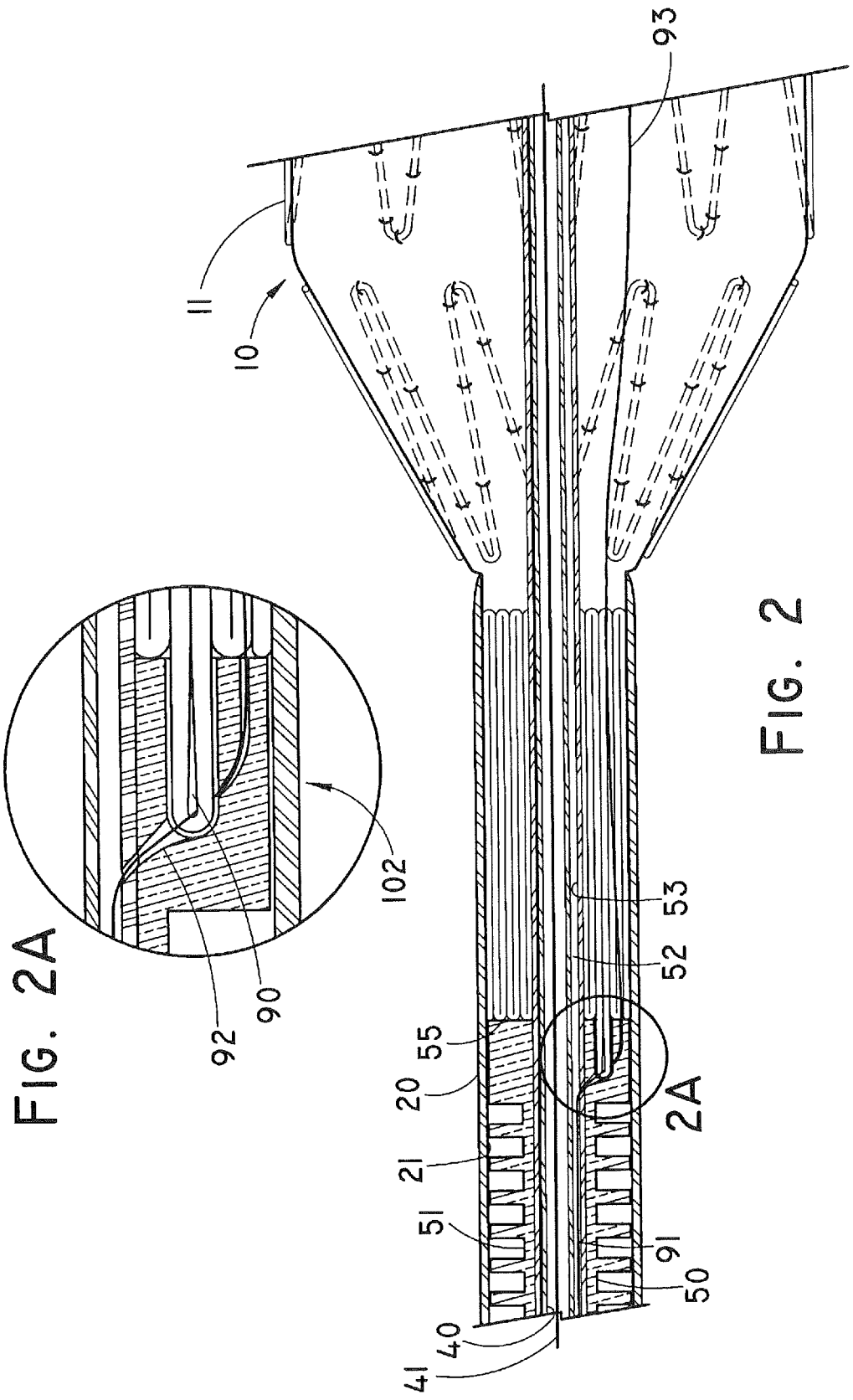
FIG. 2 is a sectional detail view of a portion of the delivery and deployment device of FIG. 1 around the proximal end of the prosthesis.
Figure 3:
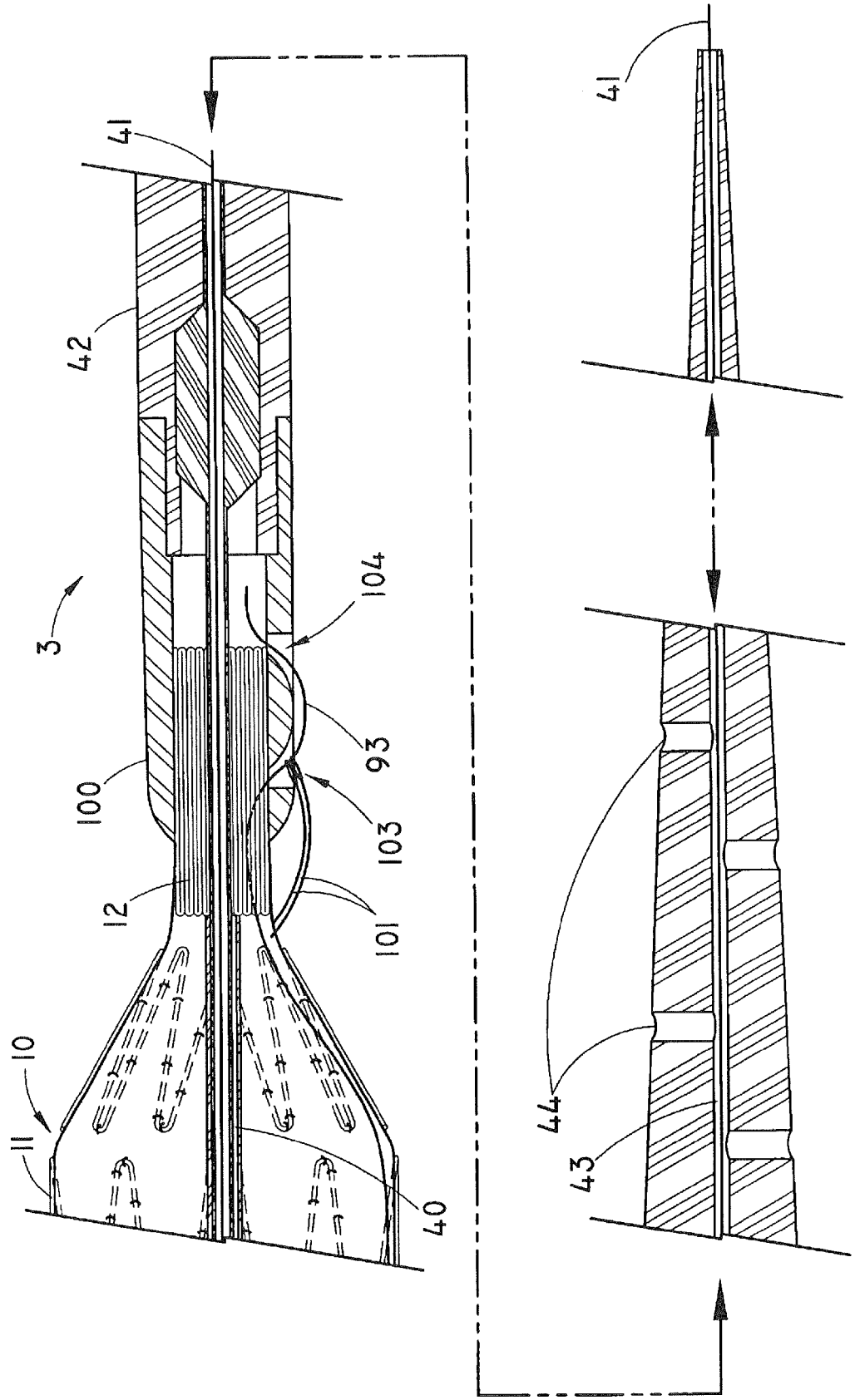
FIG. 3 is a sectional detail view of a portion of the delivery and deployment device of FIG. 1 around the distal end of the prosthesis.
Figure 11:
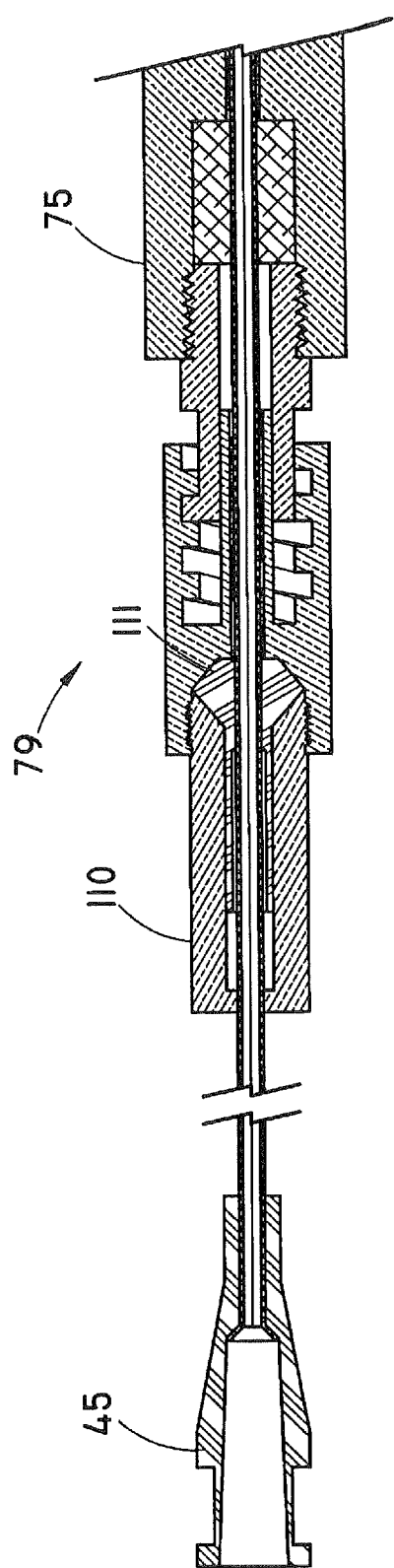
FIG. 11 is a sectional view of a portion of the delivery and deployment device of FIG. 1 around the pin vise clamp and the medical reagent introduction tube.

The delivery and deployment system shown in FIGS. 1-3 further comprises a thin walled tube or inner cannula 40. The inner cannula 40 is configured to receive a guide wire 41. The inner cannula 40 extends proximally to the proximal end of the delivery system. A flexible extension 42 is coupled to the distal end of the cannula 40, as shown in FIG. 3. The flexible extension 42 comprises an extension lumen 43 and a plurality of lateral apertures 44. The extension 42 is adapted for insertion into a body lumen. The cannula 40 terminates proximally at connection means 45, as shown in FIGS. 1 and 11. The connection means 45 is in fluid communication with the cannula 40, the extension lumen 43, and lateral apertures 44. The connection means 45 is adapted to accept a syringe and may be used to introduce reagents into the body lumen.

The cannula 40 is disposed within the lumen 21 of the sheath 20. The prosthesis 10 is radially retained over a distal portion of the cannula 40 by the sheath 20. The cannula 40 is preferably flexible so that the device can be advanced within a relatively tortuous vessel, such as a femoral artery or the aortic arch. The cannula 40 may comprise metal, for example aluminum, stainless steel, or nitinol. The cannula 40 is in mechanical communication with the flexible extension 42. This allows the operator to control the flexible extension 42 remotely during a procedure. For example, the operator can rotate or slide the flexible extension 42 relative to the prosthesis 10 by manipulating the cannula 40.

Figure 9:
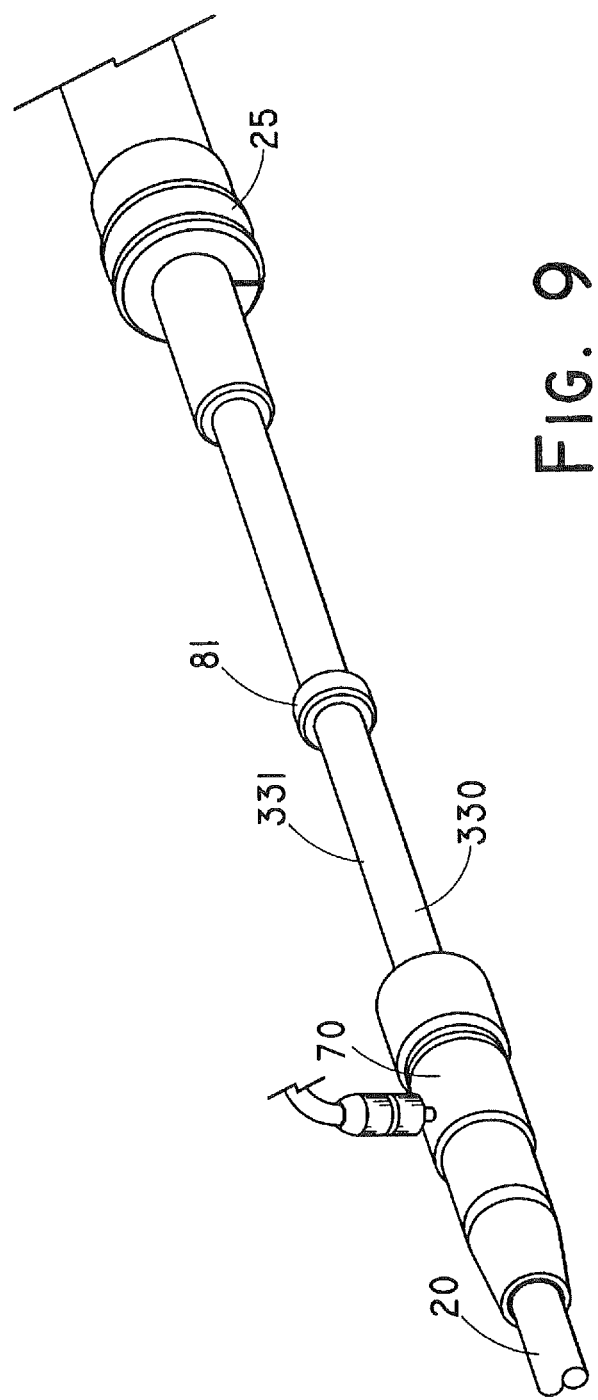
FIG. 9 is a perspective view of a medial portion of the delivery and deployment device of FIG. 1.
Figure 10:
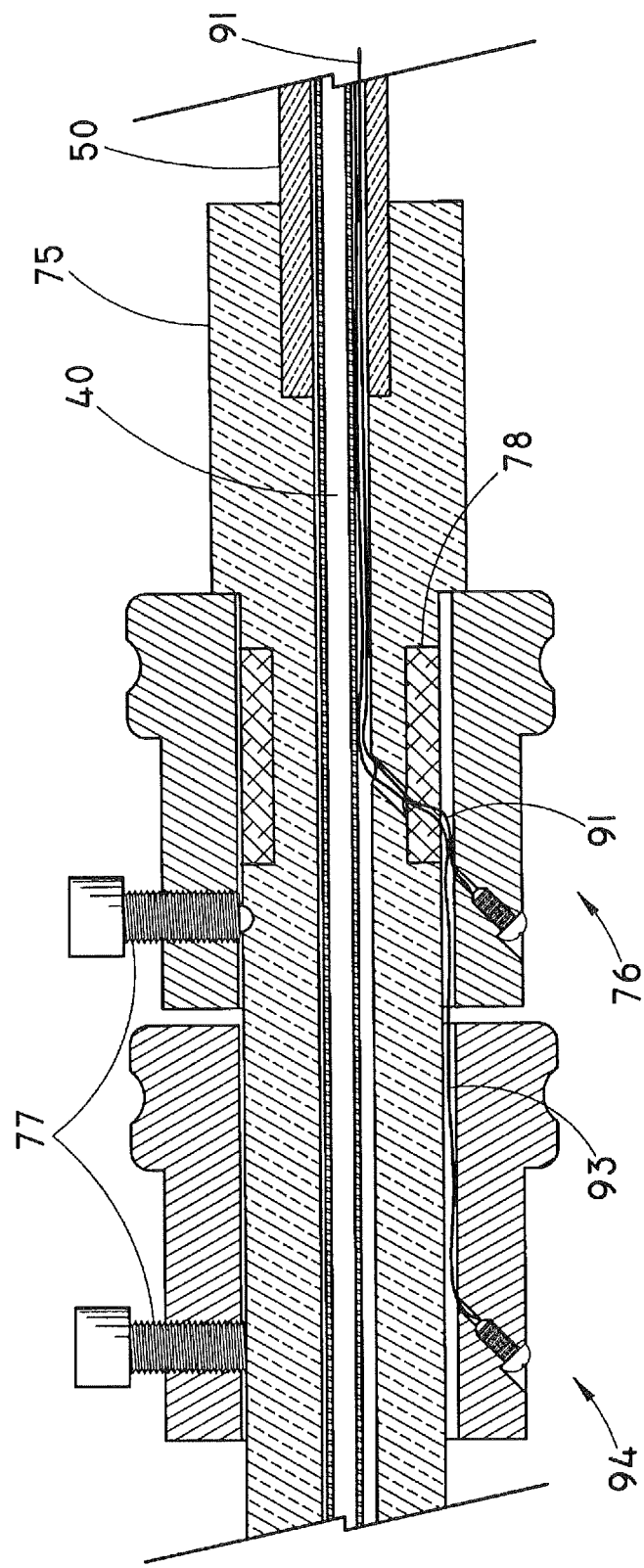
FIG. 10 is a sectional view of a portion of the delivery and deployment device of FIG. 1 around the trigger wire release mechanism.

The delivery and deployment device further comprises an elongate tubular pusher 50, as shown in FIG. 2. The pusher 50 has an exterior surface 51 and a pusher lumen 52 having an interior surface 53. The cannula 40 is slidably disposed within the lumen 52 of the pusher 50. The pusher 50 extends proximally to the manipulation region 1, as shown in FIGS. 8-10. The sheath 20 is slidably disposed over a generally distal portion of the pusher 50. The delivery and deployment system further comprises haemostatic sealing means 70, shown generally in FIG. 8, for controlling blood loss through the delivery and deployment device.

As shown in FIG. 2, the distal end of the pusher 50 is disposed adjacent the proximal end of the prosthesis 10. To deploy the prosthesis 10, the operator slides the sheath 20 proximally while applying distal pressure to the pusher 50 in the user manipulation region 1. The pusher 50 comprises a blocking element 55 that prevents the prosthesis 10 from sliding proximally with the sheath 20 when the sheath is withdrawn. As a result, the sheath 20 retracts proximally over the prosthesis 10, causing the prosthesis 10 to become exposed and to expand radially outwardly.

The pusher 50 may comprise any suitable biocompatible material, including metal or plastic. The pusher 50 may comprise a radiopaque material. Suitable materials include, but are not limited to aluminum, nitinol, nylon, polypropylene, and polyethylene. The pusher 50 preferably has high longitudinal column strength to ensure adequate energy transfer between the user and the prosthesis during deployment. The pusher 50 preferably has a high degree of flexibility and trackability. The pusher 50 is preferably configured so that the flexibility of the device over the proximal end of the prosthesis 10 generally matches the flexibility of the device over the distal end of the pusher 50 to avoid kinking in the transition therebetween.

FIGS. 5A and 5B depict one example of a pusher 150. The pusher 150 is generally tubular and has a distal end 151 and a proximal end (not shown). The pusher 150 has an exterior surface 152 and an inner lumen 157 defining an interior surface 158. Inner cannula 170 is slidably disposed within the lumen of the pusher 150. The pusher 150 is configured to transmit force from the user to the prosthesis during use. In one example, the pusher 150 comprises a slotted configuration 153 in the exterior surface 152. The slotted configuration 153 comprises fins 154 and interspaces 160 extending circumferentially from the pusher 150 along the longitudinal axis of 155 of the pusher 150.

The fins 154 comprise a radial depth 156 and a longitudinal length 159. The radial depth 156 may be generally less than the thickness of the pusher wall, defined by the pusher exterior surface 152 and pusher interior surface 158. Alternatively, the fins 154 may have a radial depth 156 that is generally equal to the thickness of the pusher wall. The radial depth 156 may be relatively uniform along the length of the pusher 150 or may vary along the length of the pusher 150. For example, the radial depth 156 at the pusher distal end 151 may approximate the thickness of the pusher wall, whereas the radial depth 156 at the pusher proximal end may be less than the thickness of the pusher wall. In one example, the radial depth 156 at the pusher distal end 151 may be about 40% to about 90% of the thickness of the pusher wall, about 50% to about 80% of the thickness of the pusher wall, about 60% to 70% of the thickness of the pusher wall, whereas the radial depth 156 at the pusher proximal end may be about 5% to about 60% of the thickness of the pusher wall, about 15% to about 50% of the thickness of the pusher wall, about 25% to about 40% of the thickness of the pusher wall. It will be apparent that the flexibility of such a pusher may generally decrease proximally along the length of the pusher.

The radial depth should be limited such that the pusher retains sufficient compressive stiffness within the pusher core to provide adequate longitudinal pushing force. In some examples, the radial depth may be determined as a function of the pusher material properties.

The fin longitudinal length 159 should be sufficiently long to provide adequate radial support against the overlying sheath while preventing radial collapse of the fin. In some examples, the fin longitudinal length 159 may be a function of the fin material strength and the radial depth of the interspace.

The slotted configuration may comprise a generally longitudinally uniform fin longitudinal length, as shown in FIGS. 5A and 5B. Alternatively, the fin longitudinal length may vary proximally with the pusher. For example, the slotted configuration may comprise a first fin longitudinal length near the distal end of the pusher that is less than a second fin longitudinal length at a position proximal of the distal end. The pusher therefore comprises a slotted configuration that has a proximally-increasing fin longitudinal length, and therefore a distally-increasing flexibility. A pusher may alternatively have a slotted configuration with a proximally-decreasing fin longitudinal length, and therefore a distally-decreasing flexibility.

The interspace 160 comprises a slot, or longitudinal void, formed in the pusher wall that can accommodate compressive stress during bending to provide flexible regions within the pusher rod. The interspace 160 may have a depth defined by the outer diameter surface to a selected radial depth.

The slotted configuration may comprise a generally longitudinally uniform interspace, as shown in FIGS. 5A and 5B. Alternatively, the interspace may vary proximally with the pusher. For example, the slotted configuration may comprise a first interspace near the distal end of the pusher that is greater than a second interspace at a position proximal of the distal end. The pusher comprises a slotted configuration that has a proximally-decreasing interspace, and therefore a distally-increasing flexibility. A pusher may alternatively have a slotted configuration with a proximally-increasing interspace, and therefore a distally-decreasing flexibility.

The interspace should be limited such that the pusher retains sufficient compressive stiffness within the pusher core to provide adequate longitudinal pushing force. In some examples, the interspace may be determined as a function of the pusher material properties. The interspace longitudinal length may also be a function of the fin longitudinal length and the pusher material strength properties. For example, if the pusher rod material is sufficiently stiff or the fin longitudinal length is sufficiently long so as to avoid collapse, then the interspace longitudinal length can be increased accordingly. The interspace longitudinal length should be selected such that the pusher core does not kink under bending when subjected to a tortuous anatomy.

In general, when a tube is bent or flexed, it will tend to deform in such a way so as to minimize the overall stress on the tube. The slotted configuration 153 acts to reduce stress in the pusher 150 so that when the pusher 150 is flexed, it will tend to bend at the interspaces 160. The slotted configuration 153 relieves tension in the tubular pusher 150 and provides a region of enhanced flexibility thereto.

The term "fin" as used herein refers to a radial rib, radial support, sheath contact rib, or the like. The term "interspace" as used herein refers to a depression, cut, groove, notch, line, perforation, aperture, or the like, or a series of depressions, cuts, grooves, notches, lines, perforations, apertures, or the like. Accordingly, a "fin" is a structural element and is not limited to any particular method or process. A slotted configuration may be provided by any mechanical, thermal, or chemical means known in the art. For example, a slotted configuration may be provided using a knife or carbide tip, by chemical etching, by laser scoring, or by molding.

The slotted configuration may comprise a dual-cut pattern, a tri-cut pattern, a quad cut pattern, or similar cut-out pattern. For example, in FIG. 6A, the pusher 180 comprises a slotted configuration 181 having a dual-cut pattern comprising fins 184 and interspaces 186. A central core 182 circumscribes the pusher lumen 183 and may provide additional stability to the pusher 180. Fins 184 extend circumferentially from the central core 182 to the pusher exterior surface 185. The central core 182 may provide enhanced durability to the pusher 180 and connecting fins 184 and further increase the pusher column strength and longitudinal pushing force. The pusher lumen 183 may accommodate, for example, trigger wires, cannulas, multiple guide wires, and injection ports. Additionally, the central core 182 may include channels or orifices 187 to also accommodate, for example, trigger wires, cannulas, multiple guide wires, and injection ports. FIG. 6B depicts a pusher 190 comprising a slotted configuration 191 having a tri-cut pattern. A central core 192 circumscribes the pusher lumen 193. Three ribs 194 extend circumferentially from the central core 192 to the pusher exterior surface 195. FIG. 6C depicts a pusher 204 comprising a slotted configuration 205 having a quad-cut pattern. A central core 206 circumscribes the pusher lumen 207. Four ribs 208 extend circumferentially from the central core 206 to the pusher exterior surface 209.

The ribs need not be oriented symmetrically around the central core, and may have any suitable configuration. For example, the ribs may be random, alternate, shift 90 degrees, shift 180 degrees, or otherwise be asymmetrical.

Although the pushers in the illustrative figures are shown with slotted configurations having two, three, or four ribs, the slotted configuration may include any suitable number of ribs. The slotted configuration need only be able to provide the functionality described herein. The specific number chosen will depend on several factors, including the type and configuration of the pusher. For example, the slotted configuration may comprise 0, 1, 2, 3, 4, 5, 6, 7, 8, or more ribs. The ribs can be arranged in any suitable configuration with respect to one another and the prosthetic valve. For example, a slotted configuration may have no ribs, the slotted configuration comprising interspaces that circumscribe the pusher central core. Fins are thereby only attached at the central core.

In FIG. 5A, the slotted configuration 153 extends proximally from the distal end 151 of the pusher 150. In FIG. 5B, the slotted configuration 173 has a distal end 174 that is disposed generally intermediate the proximal end (not shown) and distal end 176 of the pusher 175. The slotted configurations 153 and 173 relieve tension in the pushers 151 and 175, respectively, thereby making the pusher more axially flexible.

The pusher may comprise a single material along the entire length of the pusher. Alternatively, the pusher may comprise a plurality of axial regions, each region comprising a different material. For example, in FIG. 5B, the pusher 175 comprises a distal tip portion 176 and a body portion 177. The distal tip portion 176 may comprise a relatively flexible material, for example a low-durometer nylon or thermoplastic elastomer and the body portion 177 may comprise a relatively rigid material, for example a high-durometer nylon or thermoplastic elastomer. The relatively flexible material in the distal tip 176 provides the pusher 175 with enhanced flexibility over a distal portion of the pusher. The relatively rigid material in the body portion 77 provides the pusher 170 with enhanced pushability. The pusher 170 may comprise a slotted configuration 173 in the body portion 177. The slotted configuration 173 enhances the flexibility of the body portion 177 and provides a smooth transition in flexibility between the distal tip 176 and the body portion 177.

The pusher slotted configuration may comprise any suitable slotted configuration. Pusher slotted configurations include, but are not limited to, aligned slotted configurations, alternating slotted configurations, offset slotted configurations, spiral slotted configurations, and/or stepped slotted configurations. For example, FIG. 5A depicts a pusher 150 having an aligned slotted configuration 153. Fins 154a are positioned 180 degrees opposite fins 154b. Similarly, interspaces 160a are directly opposite interspaces 160b. FIG. 5B depicts a pusher 170 comprising an alternating slotted configuration 173. Fins 178a are positioned opposite interspaces 179b. Fins 178b are positioned opposite interspaces 179a.

The pushers depicted in FIGS. 5A and 5B comprise a dual cut pattern. Pushers comprising a dual-cut pattern, tri-cut pattern, quad-cut pattern, or similar may comprise any suitable slotted configuration. For example, FIG. 6C depicts an offset slotted configuration 205. The offset slotted configuration 205 comprises a quad-cut pattern, though the a pusher comprising an offset configuration may have any suitable cut pattern. Each rib 208b is offset from the adjacent ribs, for example rib 208b is offset from the rib proximal 208a and the rib distal 208c to the rib 208b. The offset 210 may be any suitable offset such that the pusher functions as described herein. The offset 210 need not be uniform between adjacent ribs, and may vary along the longitudinal length of the pusher.

Figure 6D:
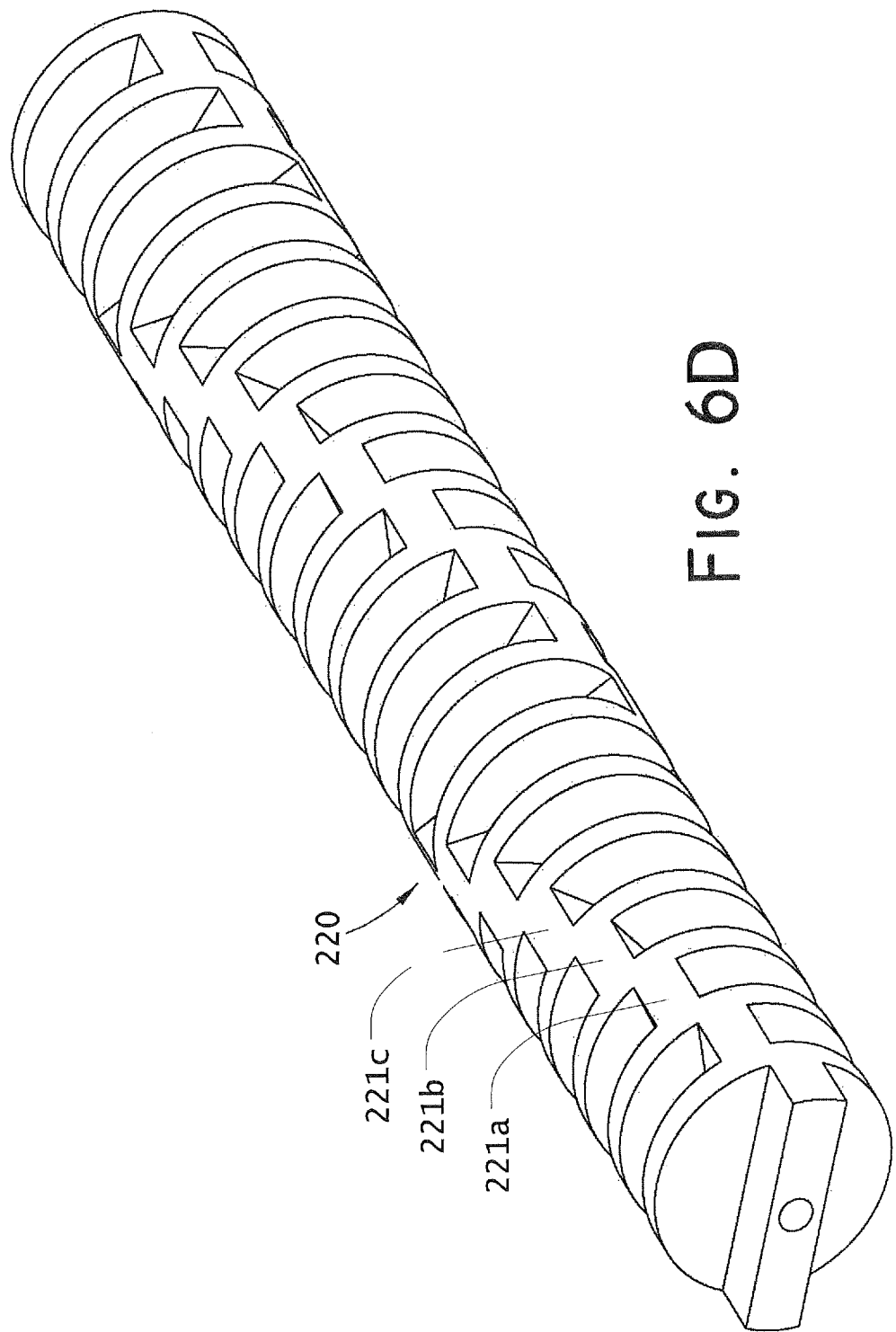
FIG. 6D is an end cross-sectional view of a pusher of a delivery system in accordance with the present invention.

FIG. 6D depicts a spiral slotted configuration 220. The spiral configuration 220 comprises a dual-cut pattern, though a pusher comprising a spiral configuration may have any suitable cut pattern. Each rib 221b is slightly offset the adjacent ribs 221a, 221c such that the ribs 221a, 221b, 221c form a spiral pattern about the pusher exterior surface.

FIGS. 7A-7B illustrate additional aspects of the delivery device. In FIG. 7A, the pusher 200 comprises a dual-cut-out slotted configuration 201 that extends longitudinally with the pusher 200. As shown in FIG. 7A, the delivery and deployment device may comprise an inner sheath 210. The inner sheath 210 is radially disposed within the lumen 202 of the pusher 200 and extends between the distal and the proximal end. The inner sheath 210 is fixedly attached to the pusher 200. The inner sheath 210 may be attached to the pusher 200 at a single point or at a plurality of points along the length of the pusher. Alternatively, the inner sheath 210 and the pusher 200 may be uniformly bonded along the length of the pusher 200. The inner sheath 210 may be formed independently of the pusher 200 and may be attached using, for example, a biocompatible adhesive or a thermal bonding technique generally known in the art. Alternatively, the inner sheath 210 may be formed generally concurrently with the pusher, for example by co-injection molding or by co-extrusion. The inner sheath 210 preferably comprises a lubricious material to decrease the friction between the cannula 211 and the pusher 200. The inner sheath 210 preferably comprises a flexible material that is more flexible than the pusher 200 so that it will not significantly impact the flexibility of the system. Accordingly, the inner sheath 210 may comprise a flexible plastic such as PTFE, polyethylene, or a synthetic rubber or a thermoplastic elastomer.

The inner sheath 210 provides a barrier between the inner cannula 211 and the pusher 200. As stated previously, the slotted configuration 201 serves as a concentration site for bending stresses imposed on the pusher 200. When the pusher 200 is flexed, the bending stress is transmitted through the pusher 200 to the cannula 211. When the pusher 200 comprises a slotted configuration 201, the stress is distributed over the pusher 200 in discrete highly concentrated regions generally associated with the slotted configuration 201. These regions of highly concentrated stress can promote damage to the cannula, including kinking. The inner sheath 210 may provide an absorptive layer between the pusher 200 and the cannula 211 and disperse the bending stresses longitudinally along the delivery and deployment device.

FIG. 7B shows another pusher 300 according to an aspect of the present disclosure. The pusher 300 comprises two slotted configurations 301, 301'. The pusher 300 comprises a first region R1 generally associated with slotted configuration 301' and a second region R2 generally associated with a slotted configuration 300. Because the first region R1 has a lower fin density than the second region R1, the first region R1 is more axially flexible than the second region R2.

FIG. 8 shows a portion of the delivery and deployment device around the proximal end of the sheath 20. The device may comprise a haemostatic device 70 that provides a haemostatic seal between the sheath 20 and the pusher 50. The haemostatic device 70 may comprise a haemostatic seal 72. In FIG. 8, a clamping collar 71 clamps the sheath 20 to the haemostatic device 70. The haemostatic seal 72 may include a silicone seal ring 73. The silicone seal ring 73 forms a haemostatic seal around the pusher 50. The haemostatic device 70 may also include a side tube 74. The side tube 74 facilitates the introduction of medical reagents between the pusher 320 and the sheath 20.

The haemostatic device 70 controls blood loss through the delivery and deployment device distal of the haemostatic seal 72. Blood loss can be controlled proximal of the haemostatic seal 72 in several ways. First, the pusher 320 may provide a haemostatic seal. Accordingly, the portion of the pusher 320 proximal of the haemostatic seal 72 may be provided without a slotted configuration. Alternatively, the portion of the pusher 320 proximal of the haemostatic seal 72 may comprise a slotted configuration 321 that has a radial depth that is generally less than the wall thickness of the pusher to prevent blood leakage through the pusher 320. Alternatively, the system may comprise an inner sheath, as described above, wherein the inner sheath is fluid-impermeable. The fluid-impermeable inner sheath provides a haemostatic seal over the entire pusher 320, including the portion of the pusher 320 proximal of the haemostatic seal 72. Accordingly, the portion of the pusher 320 proximal of the haemostatic seal 72 may comprise a slotted configuration having a thickness that is generally equal to the wall thickness of the pusher.

The delivery and deployment device may optionally comprise a limiting member 81, disposed on the proximal portion of the pusher 330, that limits the proximal travel of the sheath 20 during deployment. As shown in FIG. 9, the limiting member 81 may comprise a radial projection in the exterior surface of the pusher 330 that is configured to limit the proximal movement of the sheath 20. As the sheath 20 slides proximally over the prosthesis and the pusher 330, the sealing means 70 slides towards limiting member 81 over the slide region 331. The sheath 20 is prevented from sliding proximally when the sealing means 70 engages limiting member 81. The position of limiting member 81 may be configured so that the length of the slide region 331 is generally equal to or less than the distance between the distal end of the sheath 20 and the distal pusher end. In this way, the distal end of the pusher 330 will always be contained within the sheath 20.

As shown in FIG. 2, the delivery and deployment device may optionally comprise proximal and/or distal retention and release mechanisms for radially and/or axially retaining proximal and distal ends of the prosthesis 10. FIG. 2 illustrates a proximal prosthesis retention mechanism. The proximal retention section 102 radially and axially retains a proximal end of the prosthesis 10 during the procedure. The proximal retention section 102 may comprise the pusher, as shown in FIG. 2. Alternatively, the proximal retention section 102 may comprise a separate body coupled to the pusher 50.

The proximal end of the prosthesis 10 comprises an aperture defining a loop 90. A proximal trigger wire 91 extends through the loop 90 and through an aperture 92 in the proximal attachment section 102 into an annular region between the inner cannula 40 and the pusher 50. The proximal trigger wire 91 extends proximally through the delivery and deployment device from the proximal retention section 102 to the release wire actuation section located in the external manipulation section 1 (see FIG. 1). The trigger wire 91 couples the proximal end of the prosthesis 10 to the proximal retention section 102 during deployment to limit axial displacement of the prosthesis 10. The prosthesis 10 can be selectively released into the body lumen by disengaging the trigger wire 91 from the loop 90.

Figure 4:
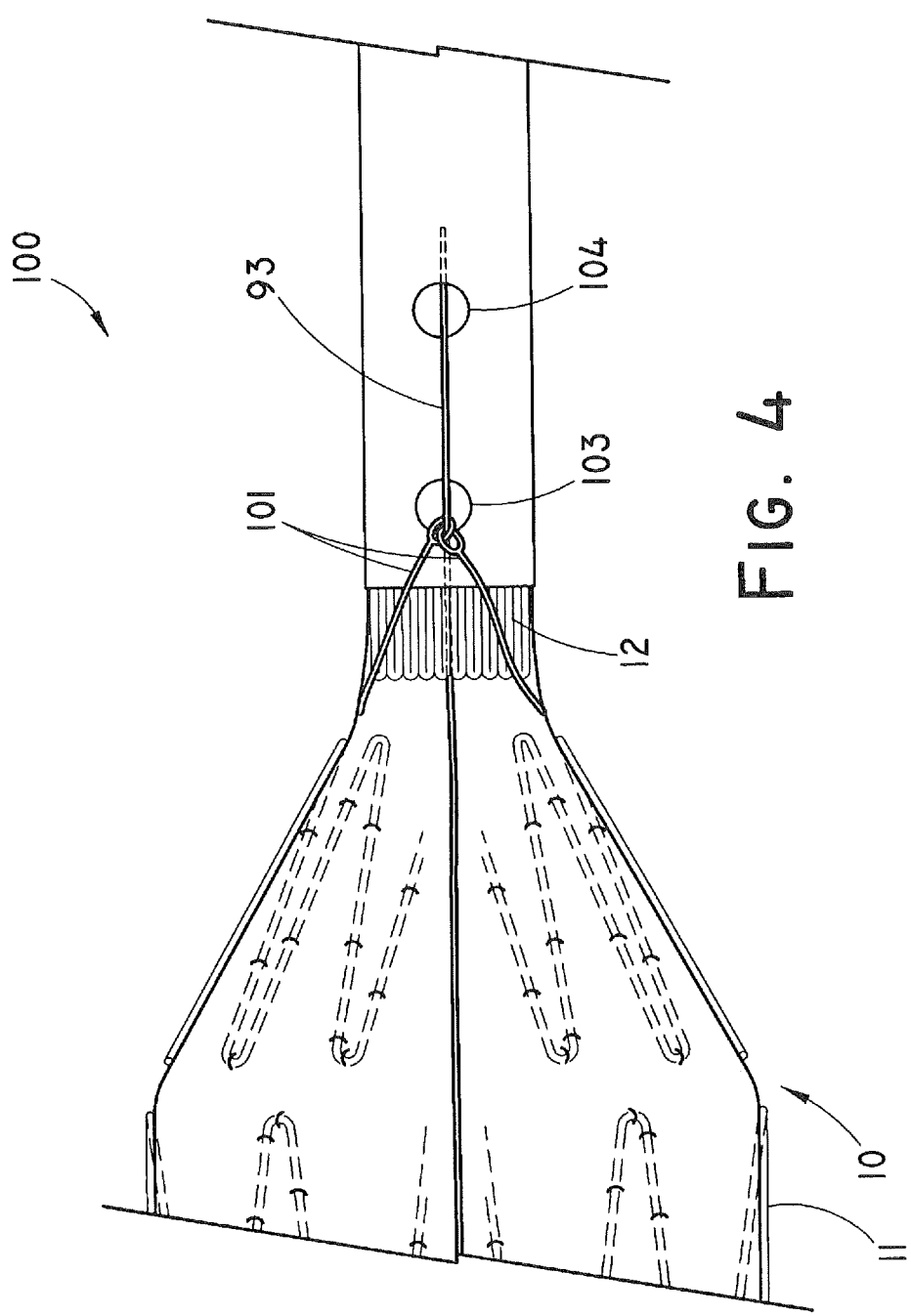
FIG. 4 is a plan view of a distal retention device of the delivery and deployment device of FIG. 1.

FIGS. 3 and 4 illustrate a distal retention mechanism. The distal attachment region 3 includes a retention device 100. The retention device 100 holds the distal end of the bare wire stent 12 in a radially compressed state. The retention device 100 may further comprise means for axially retaining the stent 12. Accordingly, the stent 12 may be retained in the retention device 100 by suture loops 101 and a distal trigger wire 93. The suture loops 101 and distal trigger wire 93 removably couple the stent 12 to the retention device 100.

FIG. 4 is a plain view of the retention device 100 showing the prosthesis 10 partially deployed, with the bare wire stent 12 still retained in a compressed state. The distal retention device 100 includes apertures 103 and 104 to accommodate the distal trigger wire 93. The suture loops 101 are coupled to the body of the prosthesis 10, and hold the stent 12 in the retention device 100 until the trigger wire 93 is removed. While the trigger wire 93 is in place, the suture loops 101 prevent the retention device 100 and the prosthesis 10 from separating. The trigger wire 93 retains the suture loops 101 against an outer surface of the retention device 100. The distal trigger wire 93 extends proximally through the delivery and deployment device from the distal retention device 100 to a release wire actuation section located in the manipulation section 1 (see FIG. 1).

As shown in FIG. 4, the suture loops 101 are attached to opposing sides of the prosthesis 10, for example separated by 90 to 180 degrees. The suture loops 101 are generally inelastic and do not stretch. Since the suture loops 101 do not stretch, they provide opposing torques, thereby preventing the prosthesis 10 from rotating within the retention device 100. This configuration differs from delivery and deployment devices that have a single point of attachment. Such devices may allow the stent to rotate within the retention device and lead to entanglement of the stent's struts. When the trigger wire 22 is removed, the suture loops 101 are free to move. The retention device 100 may then be released from the bare wire stent 12 by sliding the retention device 100 distally away from the prosthesis 10.

As shown in FIG. 10, the distal trigger wire 93 extends through the annular space between the pusher 50 and the cannula 40 to the manipulation region 1. The distal trigger wire 93 exits the annular space at a distal wire release mechanism 94. The bare wire stent 12 is released by retracting the sheath 20, removing the trigger wire 93, and then sliding the distal attachment region 3, including the retention device 100, distally away from the stent 12. Once the retention device 100 has cleared the bare wire stent 12, the stent 12 will expand. The suture loops 101, the trigger wire 93, and the distal wire release mechanism 94 form a control member to selectively release the retention device 100 from the prosthesis 10 by holding the self-expanding stent 12 in the retention device 100 until the prosthesis 10 is positioned at a desired site in the lumen.

The release wire actuation section has a body 75 that is mounted onto a proximal portion of the pusher 50, as shown in FIG. 10. The cannula 40 passes through the body 75. The proximal wire release mechanism 76 is mounted for slidable movement on the body 75. A clamping screw 77 prevents inadvertent early release of the proximal end of the prosthesis 10. Similarly, the distal wire release mechanism 94 is mounted for slidable movement on the body 75. A clamping screw 77 prevents inadvertent early release of the bare wire stent 12.

The proximal trigger wire 91 extends through the annular space between the pusher 50 and the cannula 40 to the manipulation region. The proximal trigger wire 91 exits the annular space at a proximal wire release mechanism 76. The proximal trigger wire 91 and the proximal wire release mechanism 76 form a control member to selectively release the proximal retention section 102 from the prosthesis when the prosthesis is positioned at a desired site in the lumen.

The positioning of the distal and proximal wire release mechanisms 94 and 76 is such that the distal wire release mechanism 84 must be moved before the proximal wire release mechanism 76 can be moved. Therefore, the proximal end of the prosthesis 10 cannot be released until the bare wire stent 12 has been released and anchored to the lumen. A haemostatic seal 78 is provided so the release wire 91 can extend out through the body 75 to the release mechanism 76 without unnecessary blood loss during the medical procedure.

FIG. 11 shows a proximal portion of the external manipulation section 1. A pin vise 79 is mounted onto the proximal end of the body 75. The pin vise has a screw cap 110. When screwed in, the vise jaws 111 clamp against (engage) the cannula 40. When the vise jaws 111 are engaged, the cannula 40 can only move with the body 75, and hence the cannula 40 can only move with the pusher (not shown). With the screw cap 110 tightened, the entire assembly, except for the sheath 20, can be moved as one.

Figure 12A:
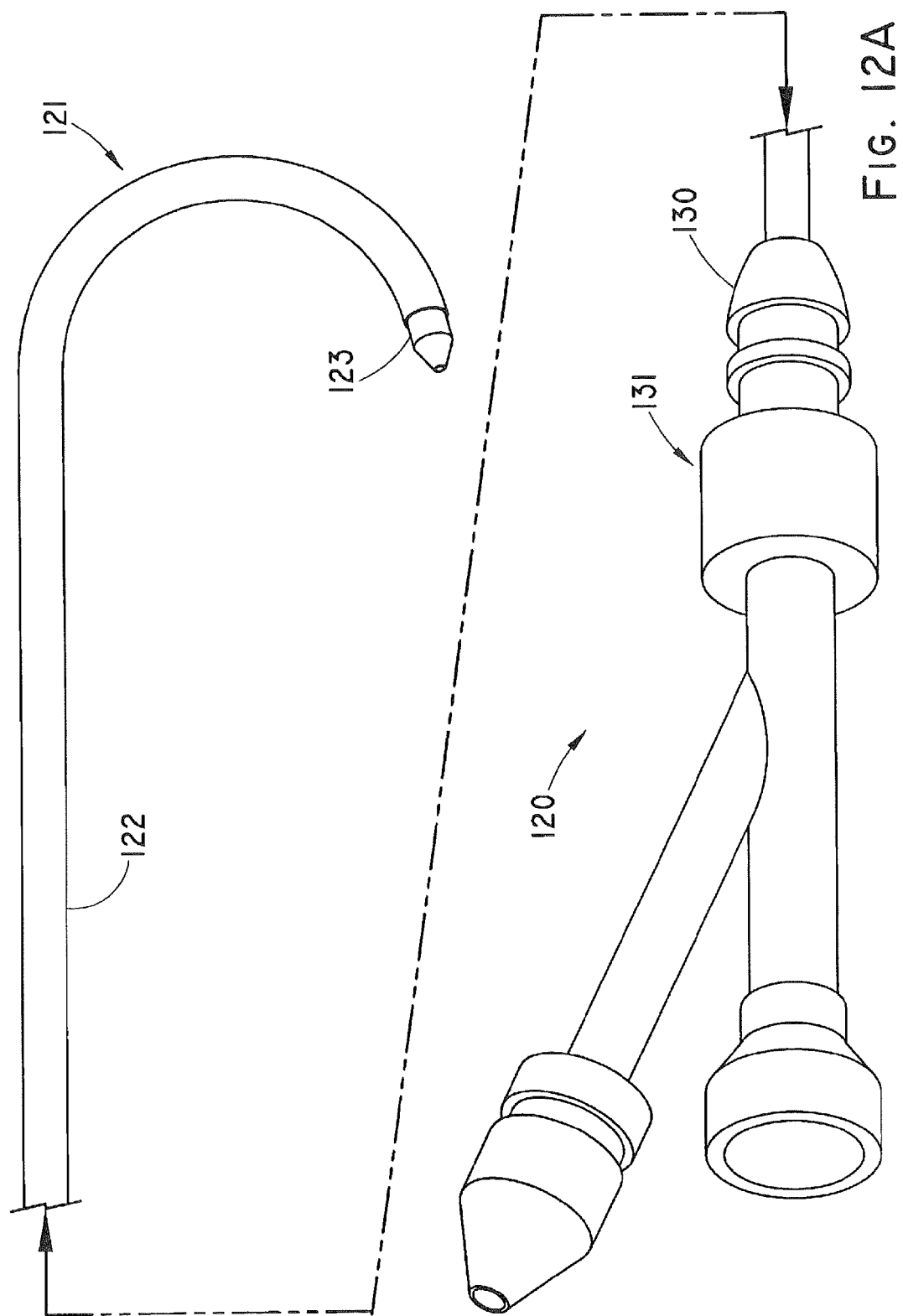
FIG. 12A is a perspective view of another delivery device of a delivery system in accordance with the present invention.
Figure 12B:
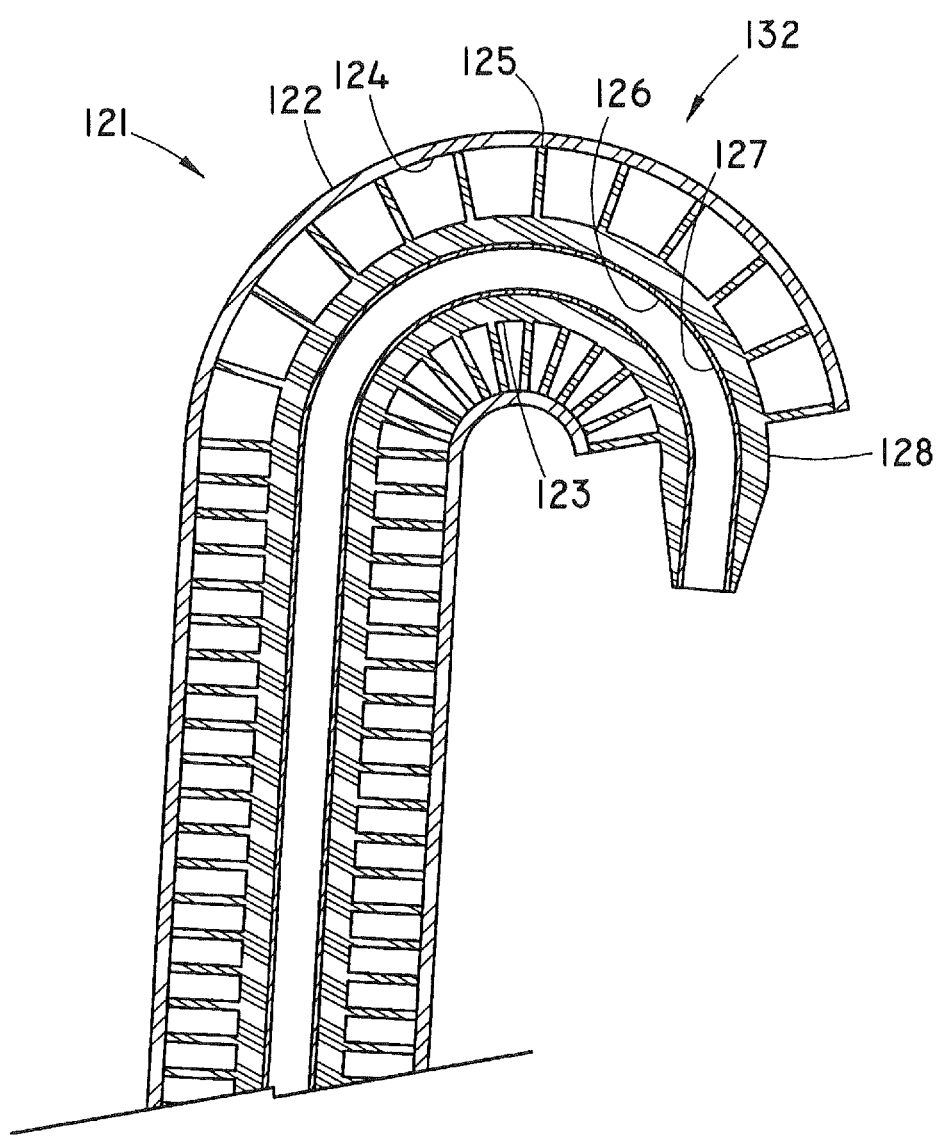
FIG. 12B is a cross-sectional view of a distal portion of the delivery device of FIG. 12A.

FIGS. 12A and 12B show another delivery system for an intraluminal medical device such as a prosthesis, a balloon catheter, a diagnostic catheter, or the like. The system includes a proximal external manipulation section 120 and a distal positioning mechanism 121. During a procedure, the distal positioning mechanism 121 will travel through the lumen to a desired deployment site, whereas the external manipulation section 120 is acted upon by a user outside of the patient to manipulate the delivery system.

The delivery system comprises a sheath 122 and a pusher 123 that is slidably and removably disposed within a lumen 124 of the sheath. The pusher 123 has an exterior surface 125 and may include a lumen 126 defining an interior surface 127, for example, for receiving a guide wire (not shown). The sheath 122 and the pusher 123 extend proximally to the external manipulation section 120. The pusher 123 provides radial and longitudinal support to the sheath 122 so that the distal end of the sheath can be intraluminally delivered to a desired location in a body lumen. Once the sheath 122 is in the desired location, the pusher 123 may be removed and additional interventional catheter devices may be delivered and deployed through the sheath lumen 124.

In the example shown in FIGS. 12A and 12B, the distal end of the pusher 123 comprises a dilator 128. During delivery of the system, the dilator 128 preferably extends distally from the sheath lumen 124 and facilitates dilation of constricted vessels as the system travels within a body lumen. The dilator 128 is preferably tapered and provides a generally smooth transition between the pusher 123 and the distal end of the sheath 122.

As shown in FIG. 12A, a haemostatic device 130, such as the device shown in FIG. 8, may be attached to the sheath 122 for providing a haemostatic seal between the sheath 122 and the pusher 123. A coupling mechanism 131, for example, a screw cap may be provided for selectively coupling the sheath 122 and the pusher 123 to prevent relative movement therebetween. The coupling mechanism 131 may be detached, for example, during insertion or retraction of the pusher 123 from the sheath lumen 122. The coupling mechanism 131 may be attached, for example, during intraluminal delivery of the system.

The delivery system may have a generally straight contour along its entire length or it may comprise an arcuate or curved contour. In the embodiment shown in FIGS. 12A and 12B, a distal portion of the delivery system has a pre-set arcuate contour, whereas a proximal portion has a generally straight contour. The proximal portion is preferably relatively rigid and has a high degree of pushability to facilitate delivery of the sheath 122 into the body lumen. Alternatively, the distal portion is preferably relatively flexible and has a high degree of trackability to facilitate tracking of the system through tortuous body luminae.

In prior art systems where the sheath has an arcuate contour, the sheath tends to straighten during insertion and retraction of the pusher, which can potentially cause bending and kinking of the sheath. This is true, even where the pusher has a corresponding pre-set contour. According to an aspect of the present disclosure, the pusher may be provided with a relatively high flexibility region over a portion corresponding with the arcuate contour to facilitate tracking during insertion and retraction of the pusher 123 within the sheath lumen 124.

The pusher 123 may be configured as described throughout the specification. As shown in FIG. 12B, the pusher 123 comprises a slotted configuration 132 in an exterior surface 125 thereof to provide flexibility to the pusher. The slotted configuration may be configured as described throughout the specification. The slotted configuration 132 preferably extends along the length of the arcuate contour, and more preferably extends proximally from the distal end of the pusher 123 over the length of the arcuate contour, as shown in FIG. 12B.

The various stages of deployment of a prosthesis 10 using a delivery and deployment device of the present invention will now be explained with reference to FIGS. 13 through 17. A guide wire 41 is introduced, for example, into the femoral artery and is advanced until the tip of the guide wire 41 is beyond the region into which the prosthesis 10 is to be deployed. The delivery assembly is then inserted through the femoral artery over the guide wire 41, and positioned by radiographic techniques. At this stage, the ends of the prosthesis 10 are retained by the distal and proximal retaining assemblies respectively and the sheath 20 is disposed over and covers the length of the prosthesis 10.

Figure 13:
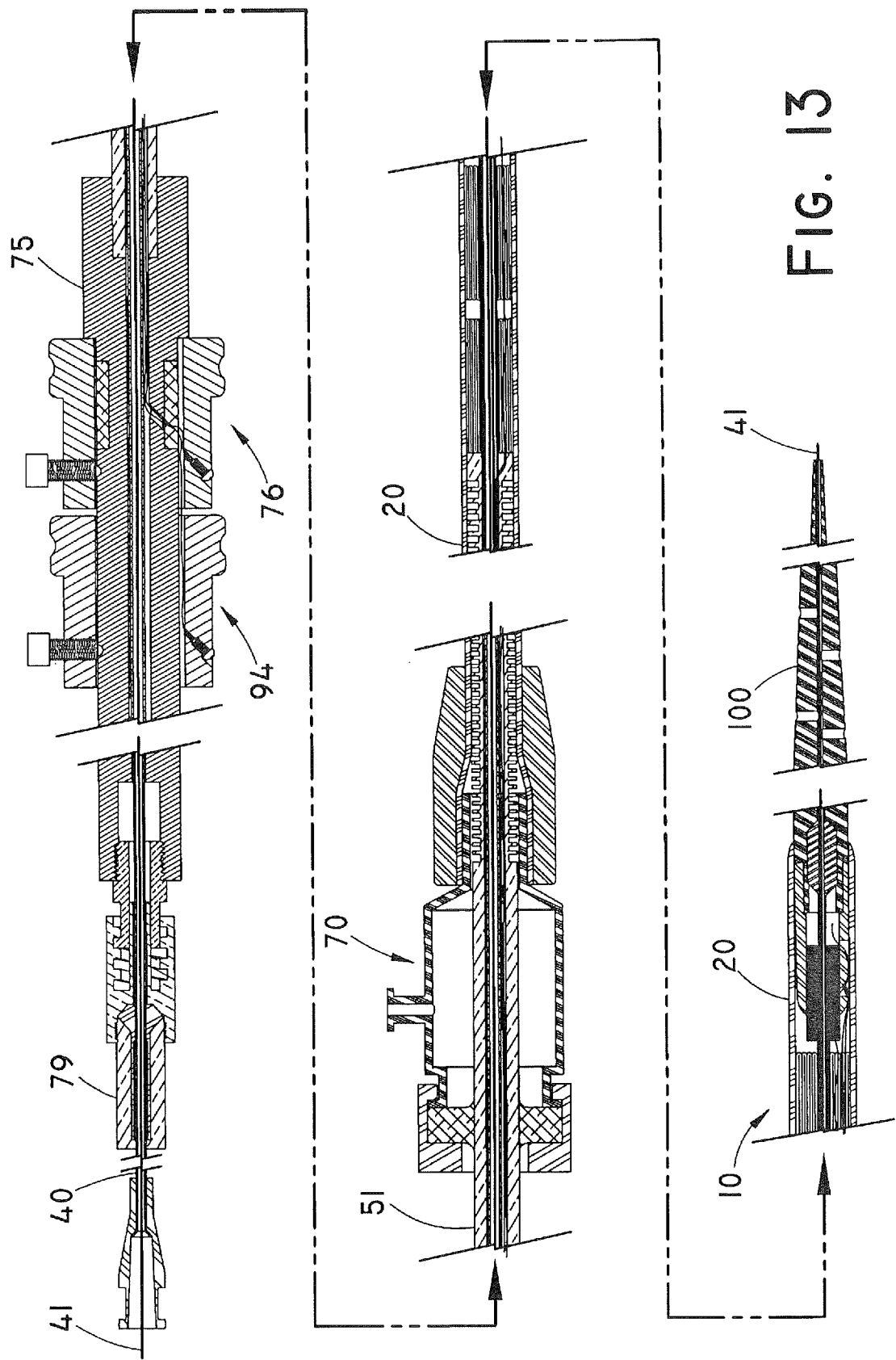
FIG. 13 is a segmented sectional view of a delivery and deployment device that is fully loaded and ready for introduction into a patient.
Figure 14:
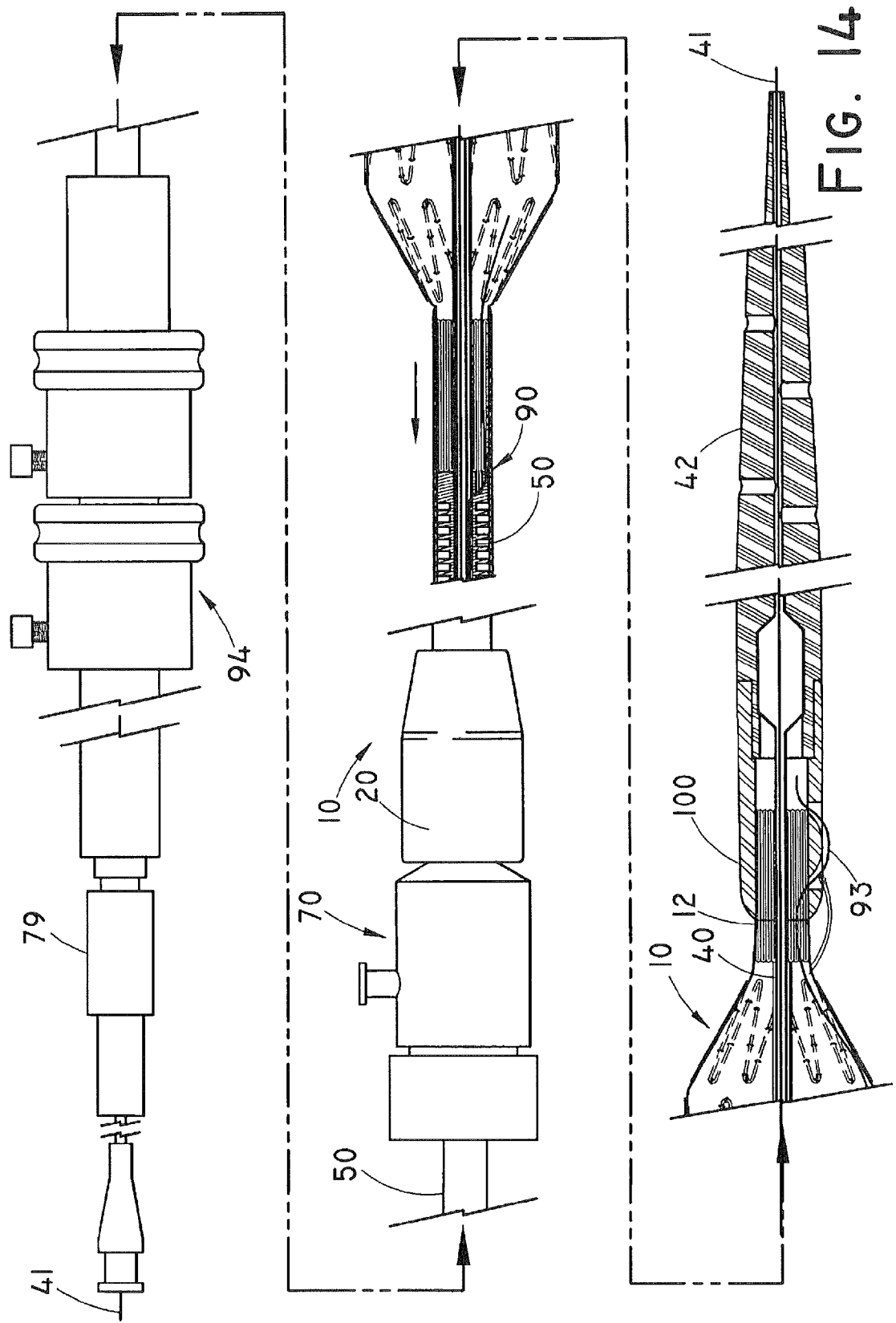
FIG. 14 is a segmented sectional view of a delivery and deployment device demonstrating the prosthesis in an initial stage of deployment.

In FIG. 13, the delivery and deployment assembly is shown fully assembled and ready for introduction into a patient. The ends of the prosthesis 10 are retained by the distal and proximal retaining assemblies respectively, while the sheath 20 compresses the middle portion of the prosthesis intermediate the ends. Once the delivery and deployment device is in a desired position for deployment of the prosthesis 10, the sheath 20 can be withdrawn to just distal of the proximal attachment section 102, as shown in FIG. 14. This action exposes the middle portion of the prosthesis 10 so that the middle portion can expand radially outwardly. The bare wire stent 12, however, is still axially and radially retained by the retention device 100. The proximal end of the prosthesis 10 is still radially and axially retained by the proximal retention section 102.

Next, the pin vise 79 is released to allow small movements of the cannula 40 with respect to the pusher 50. In this way, the prosthesis 10 may be lengthened or shortened or rotated or compressed for accurate placement in the desired location within the lumen. X-ray opaque markers (not shown) may be placed along the prosthesis 10 to assist with placement of the prosthesis.

Figure 15:
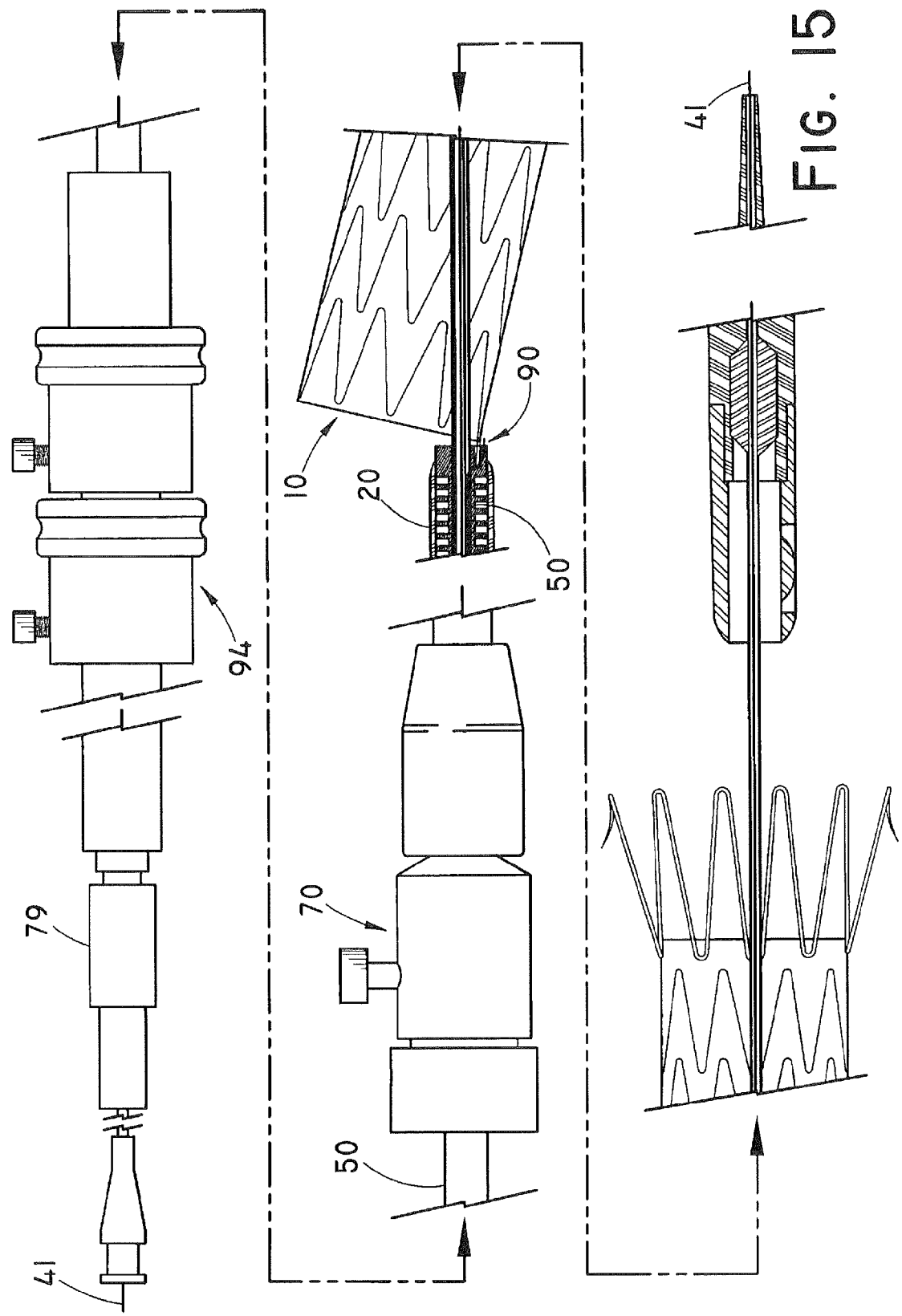
FIG. 15 is a segmented sectional view of a delivery and deployment device demonstrating the release of the prosthesis distal end during deployment.

In FIG. 15, the distal trigger wire 93 has been removed, allowing the retention device 100 to be separated from the bare wire stent 12, as explained above. At this stage, the distal trigger wire release mechanism 94 and the distal trigger wire 93 can be removed completely. The screw cap 110 of the pin vise 79 has been loosened so that the cannula 40 can be pushed in a distal direction to move the retention device 100 in a distal direction with respect to the stent 12. When the retention device 100 no longer surrounds the self-expanding stent 12 at the distal end of the prosthesis 10, the self-expanding stent 12 expands. When the self-expanding stent 12 expands, the barbs 13 grip into the walls of the lumen to hold the proximal end of the prosthesis 10 in place.

At this point, the proximal end of the prosthesis 10 is still retained by the proximal retention section 102 with the loop 90 retained therein. The sheath 20 is withdrawn to proximal of the proximal retention section 102 to allow the proximal end of the prosthesis 10 to expand. The limiting member 81 limits the travel of the sheath 20. At this point, the proximal end of the prosthesis may still be moved. Consequently, the prosthesis 10 can still be rotated or lengthened or shortened or otherwise moved for accurate positioning. Where the prosthesis 10 to be deployed is a bifurcated graft, the movement at this stage may ensure that the shorter leg is directed in the direction of the contra-iliac artery.

Figure 16:
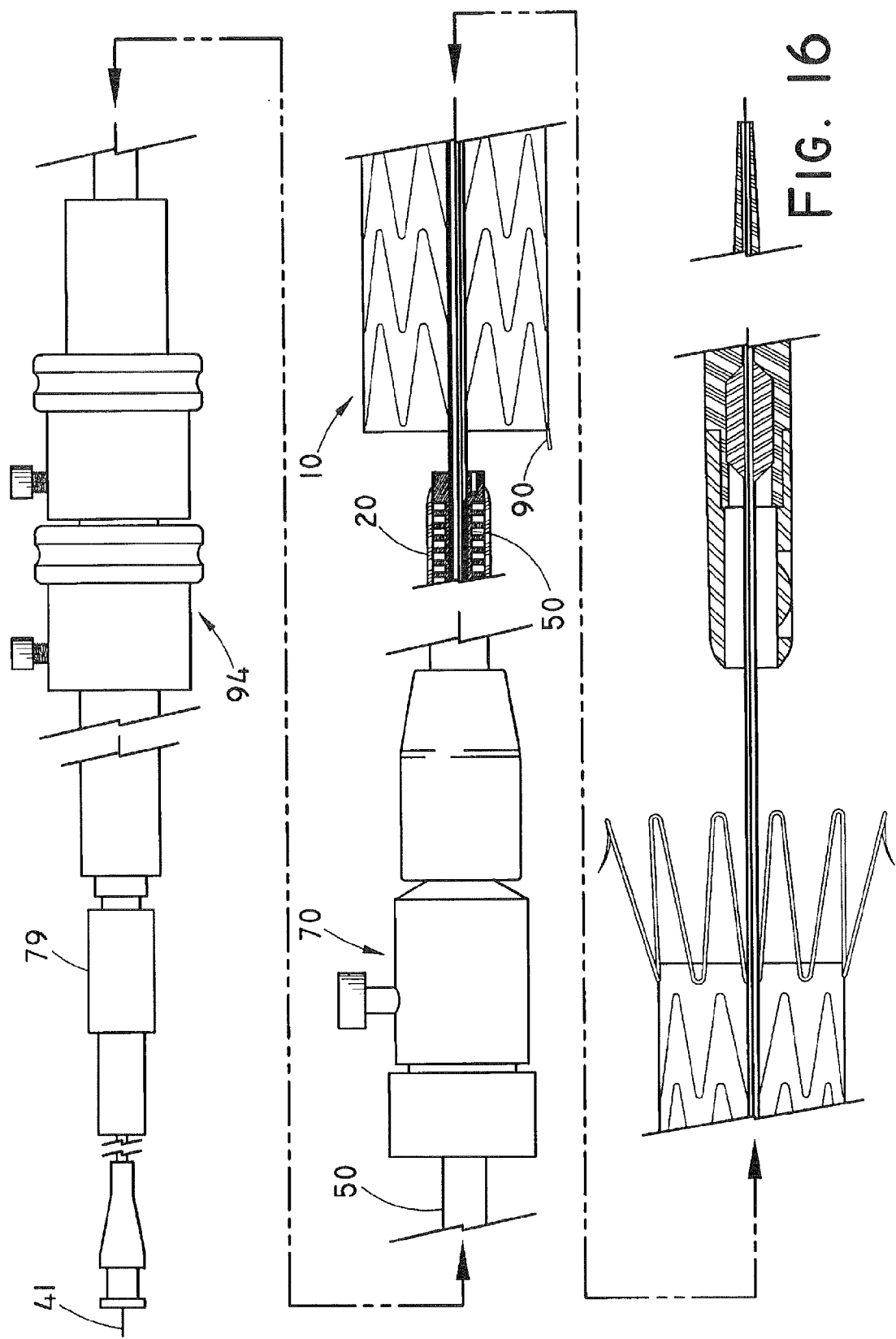
FIG. 16 is a segmented sectional view of a delivery and deployment device demonstrating the release of the prosthesis proximal end during deployment.

In FIG. 16, the proximal end of the prosthesis 10 has been released by the removal of the proximal trigger wire 91. At this stage, the proximal trigger wire release mechanism 76 and the proximal trigger wire 91 can be removed completely. This removal may be accomplished by passing the proximal wire release mechanism 76 over the pin vise 79 and the connection means 45, thereby disengaging the trigger wire 91 from the prosthesis 10. The prosthesis is now free to expand to the walls of the vessel.

Figure 17:
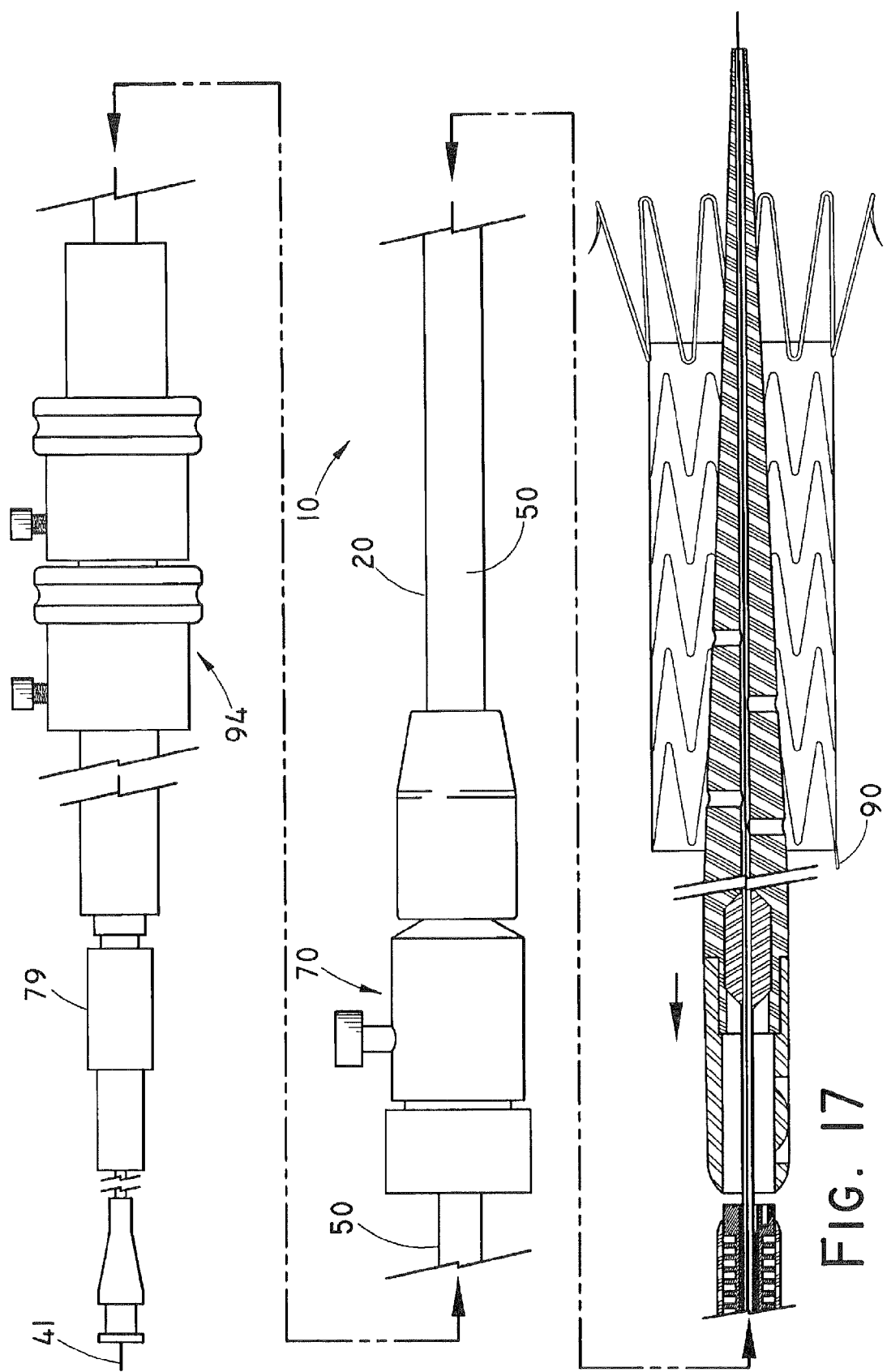
FIG. 17 is a segmented sectional view of a delivery and deployment device demonstrating the device in a configuration for withdrawal from the body lumen.

The device is now ready to be removed. The screw cap 110 of the pin vise 79 is loosened so that the cannula 40 can be moved. The cannula 40 is pulled in a proximal direction to move the retention device 100 until it comes into contact with the proximal retention section 102, as shown in FIG. 17. The pin vise 79 is then tightened so that the retention device 100 is in fixed relation to the proximal retention section 102. The entire system, including the sheath 20 may now be removed from the body lumen by pulling proximally on the system. Alternatively, the inner cannula 40, the pusher 50, and the flexible extension 42 may be removed from the sheath 20. This is done by pulling the cannula 40 proximally in relation to the sheath 20. The distal retention device 100 provides a compressive force against the pusher 50, preventing the pusher 50 from elongating or unraveling during withdrawal.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

The invention claimed is:

1. A delivery system for an intraluminal medical device, the system comprising:
    an elongate tubular sheath having a proximal end, a distal end, and a sheath lumen;
    an elongate tubular pusher slidably disposed within the sheath lumen, the pusher having a proximal end, a distal end, an exterior surface, a lumen defining an interior surface, and a central core circumscribing the pusher lumen;
    the pusher exterior surface comprising a slotted configuration having a plurality of fins and a plurality of interspaces separating the fins, where a first interspace has a width different than a second interspace, and
    where there is a varying radial depth within one of the interspaces, wherein the radial depth is defined as the depth from the pusher exterior surface to the central core.

2. The system according to claim 1, the fins extending substantially circumferentially around the pusher.

3. The system according to claim 1, at least two of the fins or the interspaces having a uniform longitudinal length.

4. The system according to claim 1, where a first fin has a width different than a second fin at different parts of the pusher.

5. The system according to claim 4, where a width of the first fin is greater than a width of the second fin, and where the first fin is located proximal to the second fin.

6. The system according to claim 1, where the plurality of fins comprise a radial depth that is less than or equal to a thickness of the pusher wall defined by the interior and exterior surfaces of the pusher.

7. The system according to claim 1, the fins having a radial depth which varies along a length of the pusher.

8. The system according to claim 1, where the plurality of fins has a radial depth at the pusher distal end between about 40% and about 90% of a thickness of the pusher wall.

9. The system according to claim 8, where the plurality of fins has a radial depth at the pusher proximal end between about 5% and about 60% of a thickness of the pusher wall.

10. The system according to claim 1, the slotted configuration comprising a first slotted configuration at a first longitudinal position along the pusher and a second slotted configuration at a second longitudinal position along the pusher, the second slotted configuration being different from the first slotted configuration.

11. The system according to claim 1, the exterior surface of the pusher having a slotted configuration over only a part of its length.

12. The system according to claim 11, where the slotted configuration extends proximally from the distal end of the pusher.

13. The system according to claim 1, the slotted configuration comprising no ribs, one rib, two ribs, three ribs, or four ribs.

14. The system according to claim 1, the slotted configuration comprising at least one rib having at least one channel therethrough.

15. The system according to claim 1, where the slotted configuration is selected from the group consisting of aligned slotted configurations, alternating slotted configurations, offset slotted configurations, spiral slotted configurations, and stepped slotted configurations.

16. The system according to claim 1, the pusher comprising a plurality of axial regions, the regions comprising materials with different flexibility.

17. The system according to claim 1, the pusher comprising a first material along a first portion thereof, and a second material along a second portion thereof, the first material being more flexible than the second material, and where the second portion of the pusher comprises an exterior surface having a slotted configuration.

18. The system according to claim 1, further comprising a radially-expandable intraluminal prosthesis disposed in a compressed configuration within a distal portion of the sheath lumen, where the pusher is configured to push the prosthesis distally within the sheath lumen when the sheath is slid proximally in relation thereto.

19. A delivery system for an intraluminal medical device, the system comprising:
    an elongate tubular sheath having a proximal end, a distal end, and a sheath lumen;
    an elongate tubular pusher slidably disposed within the sheath lumen, the pusher having a proximal end, a distal end, an exterior surface, a lumen defining an interior surface, and a central core circumscribing the pusher lumen;
    the pusher exterior surface comprising a slotted configuration having a plurality of fins and a plurality of interspaces separating the fins,
    where there is a varying radial depth within one of the interspaces, wherein the radial depth is defined as the depth from the pusher exterior surface to the central core.

20. A delivery system for an intraluminal medical device, the system comprising:
    an elongate tubular sheath having a proximal end, a distal end, and a sheath lumen;
    an elongate tubular pusher slidably disposed within the sheath lumen, the pusher having a main longitudinal axis, a proximal end, a distal end, an exterior surface, a lumen defining an interior surface, and a central core circumscribing the pusher lumen;
    the pusher exterior surface comprising a slotted configuration having a plurality of fins and a plurality of interspaces separating the fins,
    where at least one interspace is defined by a flat inner boundary, having a width along the main longitudinal axis, that extends continuously between first and second locations along a circumferential outer perimeter of the pusher.

* * * * *